(12) United States Patent
Okada et al.

(10) Patent No.: US 9,809,531 B2
(45) Date of Patent: Nov. 7, 2017

(54) PRODUCTION METHOD OF FATTY ACID ESTER

(71) Applicant: Kao Corporation, Tokyo (JP)

(72) Inventors: Nobuhiko Okada, Wakayama (JP); Katsutoshi Yamamoto, Wakayama (JP); Taichi Homma, Haga-gun (JP); Kazuyuki Harima, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/510,943

(22) PCT Filed: Nov. 17, 2015

(86) PCT No.: PCT/JP2015/082810
§ 371 (c)(1),
(2) Date: Mar. 13, 2017

(87) PCT Pub. No.: WO2016/080550
PCT Pub. Date: May 26, 2016

(65) Prior Publication Data
US 2017/0275231 A1    Sep. 28, 2017

(30) Foreign Application Priority Data

Nov. 20, 2014  (JP) ................................ 2014-235263

(51) Int. Cl.
| | | |
|---|---|---|
| C07C 51/00 | (2006.01) | |
| C07C 67/60 | (2006.01) | |
| C07C 69/30 | (2006.01) | |
| B01J 23/78 | (2006.01) | |
| B01J 37/02 | (2006.01) | |
| B01J 35/10 | (2006.01) | |

(52) U.S. Cl.
CPC .............. *C07C 67/60* (2013.01); *B01J 23/78* (2013.01); *B01J 35/1038* (2013.01); *B01J 37/0215* (2013.01); *C07C 69/30* (2013.01)

(58) Field of Classification Search
CPC ...................................................... C07C 67/00
USPC ........................................................ 554/163
See application file for complete search history.

(56) References Cited

U.S. PATENT DOCUMENTS 5,254,705 A * 10/1993 Hattori .................. C07C 29/149
502/33
2007/0191650 A1    8/2007 Harima et al.
2010/0320123 A1   12/2010 Wu et al.

FOREIGN PATENT DOCUMENTS

| EP | 0 985 448 A1 | 3/2000 | |
|---|---|---|---|
| EP | 0985448 A1 * | 3/2000 | ............ B01J 23/755 |
| EP | 1 813 593 A2 | 8/2007 | |
| JP | 2004-277597 A | 10/2004 | |
| JP | EP 1813593 A2 * | 8/2007 | ........... C07C 29/149 |
| JP | 2007-224272 A | 9/2007 | |
| JP | 2009-523598 A | 6/2009 | |
| JP | 2009-255047 A | 11/2009 | |
| WO | WO 02/100541 A1 | 12/2002 | |
| WO | WO02100541 A1 * | 12/2002 | |

OTHER PUBLICATIONS

International Search Report issued in PCT/JP2015/082810 (PCT/ISA/210), dated Feb. 29, 2016.
Written Opinion of the International Searching Authority issued in PCT/JP2015/082810 (PCT/ISA/237), dated Feb. 29, 2016.

\* cited by examiner

*Primary Examiner* — Deborah D Carr
(74) *Attorney, Agent, or Firm* — Birch, Stewart, Kolasch & Birch, LLP

(57) ABSTRACT

A method for producing a fatty acid ester through desulfurization of sulfur from a fatty acid ester using a catalyst, wherein the catalyst carries a catalyst metal on a support,
(a) the catalyst contains as the catalyst metal one or more elements selected from the elements of group 9, group 10 and group 11 of the periodic table,
(b) the total pore volume of the catalyst is 0.05 mL/g or more, and
(c) the volume of pores with a pore size of 0.1 μm or more and 500 μm or less is 50% or more of the total pore volume of the catalyst. A desulfurization method using the desulfurization and a method for producing an alcohol through hydrogenation of the fatty acid ester obtained through the desulfurization are also provided.

17 Claims, No Drawings

PRODUCTION METHOD OF FATTY ACID ESTER

FIELD OF THE INVENTION

The present invention relates to a method for producing a fatty acid ester with a low sulfur content and a desulfurization method of a fatty acid ester, and a method for producing an alcohol by using a fatty acid ester obtained by these methods as the raw material.

BACKGROUND OF THE INVENTION

Fatty acid esters generally contain at least several milligrams per kilogram to several tens of milligrams per kilogram of sulfur components. Here, fatty acid esters mean esters of a fatty acid and glycerin (triglycerides, diglycerides and monoglycerides), esters of a fatty acid and a monohydric alcohol having 1 to 22 carbon atoms (fatty acid alcohol esters) and the like. When an alcohol is produced through hydrogenation of such a fatty acid ester in the presence of a catalyst for ester reduction, sulfur components contained in the fatty acid ester act as catalytic poisons of the reduction catalyst and reduce the catalytic activity markedly. Since the catalyst life becomes very short, it is necessary to replace the catalyst with a new one frequently, and the decrease in the operating ratio of the facility and the like are unavoidable.

As a method for removing sulfur components from a fatty acid ester, JP-A-2007-224272 discloses a method in which an adsorbent containing a metal such as Ni or Cu is used and a sulfur-containing compound is chemically hydrocracked in a hydrogen atmosphere and adsorbed to the adsorbent.

In the field of petrochemistry, desulfurization catalysts containing cobalt, molybdenum, nickel or the like as the main component are used. In order to improve the desulfurization activity for each of hydrogenation desulfurization of hydrocarbon oil in JP-A-2004-277597 and hydrogenation desulfurization of naphtha in JP-A-2009-523596, attempts have been made to regulate the mean pore diameter of the catalyst to be 6 to 15 nm or regulate the median pore size of the catalyst to fall within the range of 15 to 200 nm.

JP-A-2009-255047 discloses a honeycomb structure which is formed by integral molding of a honeycomb member used for treating exhaust gas from an internal-combustion engine and inorganic fibers. The pores of 0.005 to 0.03 µm in the honeycomb structure mainly contribute to the removal of chemically harmful substances, and the pores with a pore size of 1 to 50 µm reduce the pressure loss and increase the collection efficiency of PM (particulate matters).

SUMMARY OF THE INVENTION

Although JP-A-2007-224272 describes that the pores with a diameter of 20 to 200 nm in the adsorbent are effective for desulfurization of a fatty acid ester, a pore diameter in this range is not sufficient from the viewpoint of improving the diffusion of the reactive substrate, and the catalyst metal in the interior of the pores of the adsorbent cannot be used effectively enough. Thus, there are problems in that the catalytic activity per weight of the catalyst metal is low and the maintenance rate of the catalytic activity is also low. The adsorbent described in JP-A-2007-224272 also has its drawback since the pore size cannot be 200 nm or more from the viewpoint of the strength of the adsorbent.

The fatty acid ester of the present invention is a bulky molecule with higher polarity than kerosene, light oil and the like which are used in the field of petrochemistry to which JP-A-2004-277597 and JP-A-2009-523596 pertain, and it is believed that the techniques of the field of petrochemistry cannot be applied directly. Moreover, a pore size in the ranges described in JP-A-2004-277597 and JP-A-2009-523596 is not sufficient enough to remove sulfur components from a fatty acid ester.

With respect to the honeycomb structure described in JP-A-2009-255047, pores that contribute to the removal of chemically harmful substances are those with a pore diameter in the range of 0.005 to 0.03 µm. It is merely disclosed that pores with a pore diameter of 1 to 15 µm and those with a pore diameter of 15 to 50 µm are capable of keeping the pressure loss low and increasing the collection efficiency of PM, and this disclosure does not suggest the diffusion of reaction products in the interior of the catalyst. Accordingly, pores with a sufficient size for chemically removing sulfur components from a fatty acid ester are not disclosed.

The present invention provides: a method for producing a fatty acid ester with a low sulfur content from a raw material fatty acid ester more efficiently by improving the catalytic activity per unit mass of the catalyst metal contained in the catalyst used for desulfurization of sulfur from the fatty acid ester and by improving the maintenance rate of the catalytic activity; and a method for producing an alcohol by using a fatty acid ester obtained by this production method as the raw material. In this regard, the catalytic activity here means the rate of desulfurization in the presence of the catalyst of the present invention, and specifically, the catalytic activity can be represented by the decrease rate of the sulfur content in the fatty acid ester.

The present invention relates to a method for producing a fatty acid ester through desulfurization of sulfur from a raw material fatty acid ester using a catalyst, wherein the catalyst carries a catalyst metal on a support, (a) the catalyst contains as the catalyst metal one or more elements selected from the elements of group 9, group 10 and group 11 of the periodic table, (b) the total pore volume of the catalyst is 0.05 mL/g or more, and (c) the volume of pores with a pore size of 0.1 µm or more and 500 µm or less is 50% or more of the total pore volume of the catalyst.

Moreover, the present invention provides a desulfurization method using the desulfurization and a method for producing an alcohol through hydrogenation of the fatty acid ester obtained through the desulfurization.

The present invention uses a catalyst which contains as a catalyst metal one or more elements selected from the elements of group 9, group 10 and group 11 of the periodic table and has a total pore volume of 0.05 mL/g or more and in which the volume of pores with a pore size of 0.1 µm or more and 500 µm or less is 50% or more of the total pore volume, thereby improving the catalytic activity per mass of the catalyst metal and also the maintenance rate of the catalytic activity. As a result, a fatty acid ester with a low sulfur content can be produced efficiently from a raw material fatty acid ester, and an alcohol can be produced efficiently by using a fatty acid ester obtained by this production method as the raw material.

It is not clear why the catalytic activity per mass of the catalyst metal improves and the maintenance rate of the catalytic activity also improves when a catalyst with a specific pore structure which meets the conditions of the present invention is used, but it is believed as follows. That is, in the conventional techniques, it has been believed that smaller pores than the pores of the catalyst of the present invention were effective for desulfurization of a fatty acid ester. However, the pore sizes of the conventional catalysts are insufficient from the viewpoint of improving the diffusion of the reactive substrate. As in the present invention, by using a catalyst with a specific pore structure of a size which is by far larger than those of the conventional techniques, diffusion of the reactive substrate into the interior of the catalyst pores can be promoted, and the catalyst metal in the interior of the catalyst pores can be used effectively enough. Moreover, it is believed that, with a catalyst with a specific pore structure such as the catalyst of the present invention, the products generated through hydrogenolysis of the sulfur-containing compounds rapidly flow out of the interior of the catalyst pores, and thus the catalytic activity is prevented from decreasing as compared to the conventional techniques. It is believed that, as a result, the catalytic activity per mass of the catalyst metal improves, and the maintenance rate of the catalytic activity also improves.

EMBODIMENTS OF THE INVENTION

<Fatty Acid Ester>

The fatty acid ester which is used in the present invention as the raw material is a fatty acid alcohol ester which is an ester of a fatty acid and a monohydric alcohol having 1 or more and 22 or less carbon atoms, a fat or oil, or the like.

Examples of fats and oils include animal fats and oils such as beef fat and fish oil, or a vegetable fats and oils such as palm kernel oil, coconut oil, palm oil, soybean oil and rape oil. Among them, from the viewpoint of usability of reaction products as surfactants, those derived from vegetable fats and oils are preferable, those derived from one or more kinds of fats and oils selected from palm kernel oil, coconut oil and palm oil are more preferable, and those derived from palm kernel oil or coconut oil are further preferable. From the same viewpoint, the carbon number of the constituent fatty acid of the fat or oil is preferably 8 or more, and preferably 22 or less, and more preferably 18 or less.

The fatty acid alcohol ester can be obtained through transesterification of glycerides in the fat or oil and a monohydric alcohol having 1 or more and 22 or less carbon atoms or through esterification of a fatty acid obtained through hydrolysis of the fat or oil and a monohydric alcohol having 1 or more and 22 or less carbon atoms. Accordingly, from the viewpoint of usability of reaction products as surfactants, and from the viewpoint of availability of raw materials, the constituent fatty acid of the fatty acid alcohol ester is preferably a fatty acid derived from vegetable fats and oils, more preferably a fatty acid derived from one or more kinds of fats and oils selected from palm kernel oil, coconut oil and palm oil, and further preferably a fatty acid derived from palm kernel oil or coconut oil. From the same viewpoint, the carbon number of the constituent fatty acid is preferably 8 or more, and preferably 22 or less, and more preferably 18 or less. Moreover, from the same viewpoint, the constituent fatty acid preferably has a linear or branched, saturated or unsaturated hydrocarbon group, more preferably has a linear, saturated or unsaturated hydrocarbon group and further preferably has a linear, saturated hydrocarbon group.

From the viewpoint of improving the productivity, the monohydric alcohol having 1 or more and 22 or less carbon atoms is preferably a lower monohydric alcohol having 1 or more and 4 or less carbon atoms, more preferably methanol or ethanol, and further preferably methanol.

The transesterification and the esterification can be conducted by known methods. Any of continuous, batch and semi-batch reaction processes can be used for the reaction, but when a large amount of ester is produced, a continuous process is advantageous. Examples of the catalyst for the transesterification include a homogeneous alkali catalyst such as sodium hydroxide, potassium hydroxide and sodium alcoholate or a solid catalyst such as an ion exchange resin, hydrous zirconium oxide, aluminum phosphate, sulfuric acid-on-zirconia and titanosilicate.

When the transesterification of a fat or oil is conducted using a homogeneous alkali catalyst, from the viewpoint of reducing the amount of by-products, the fatty acid contained in the fat or oil is converted to an ester with a monohydric alcohol having 1 or more and 22 or less carbon atoms preferably using an acid catalyst such as sulfuric acid and para-toluenesulfonic acid before the transesterification. The reaction temperature of the transesterification of the oil using a homogeneous alkali catalyst is, from the viewpoint of reactivity, preferably 30° C. or higher, and more preferably 40° C. or higher and, from the viewpoint of the yield of the fatty acid alcohol ester, preferably 90° C. or lower, and more preferably 80° C. or lower. The reaction pressure of the transesterification of the fat or oil using a homogeneous alkali catalyst in terms of the gauge pressure is, from the viewpoint of reactivity, preferably atmospheric pressure or higher and 0.5 MPa or lower, and more preferably atmospheric pressure.

The amount by mole of the monohydric alcohol having 1 or more and 22 or less carbon atoms used for the transesterification is, based on the mole of the glycerides in the fat or oil, from the viewpoint of reactivity, preferably 1.5 times or more, more preferably 3 times or more, and further preferably 6 times or more and, from the economic viewpoint, preferably 15 times or less, and more preferably 12 times or less.

As the fatty acid ester, a fatty acid ester with a sulfur content before desulfurization of 0.01 mg/kg or more and 50 mg/kg or less is generally used. The sulfur content in the fatty acid ester is, from the viewpoint of the availability of raw materials, preferably 0.01 mg/kg or more and, from the viewpoint of the durability of the catalyst of the present invention, preferably 30 mg/kg or less, and more preferably 10 mg/kg or less. Examples of the sulfur-containing compounds which can be removed efficiently by a method using the catalyst of the present invention are thiols, sulfides, thiocarboxylic acids and aromatic sulfur-containing compounds such as thiophenes.

<Catalyst>

The catalyst used in the present invention carries a catalyst metal on a support and contains as the catalyst metal one or more elements selected from the elements of group 9, group 10 and group 11 of the periodic table. The total pore volume of the catalyst is 0.05 mL/g or more, and the volume of pores with a pore size of 0.1 μm or more and 500 μm or less is 50% or more of the total pore volume. In the following description, the catalyst metal means an element which constitutes a substance in the catalyst having functions of hydrogenolyzing sulfur-containing compounds in a fatty acid ester, adsorbing the generated sulfur and removing the sulfur-containing compounds from the fatty acid ester. Moreover, a compound containing the catalyst metal is called a catalyst metal compound.

The total pore volume of the catalyst used in the present invention is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, 0.05 mL/g or more, preferably 0.15 mL/g or more, more preferably 0.5 mL/g or more, further preferably 0.7 mL/g or more, furthermore preferably 0.9 mL/g or more, and furthermore preferably 1 mL/g or more and, from the viewpoints of improving the efficiency of contact between the catalyst metal and sulfur-containing compounds in the interior of the catalyst, and thereby improving the catalytic activity, and of improving the strength of the catalyst, preferably 10 mL/g or less, more preferably 4 mL/g or less, furthermore preferably 2.5 mL/g or less, and furthermore preferably 1.6 mL/g or less.

The volume of pores with a pore size of 0.1 μm or more and 500 μm or less in the catalyst used in the present invention is, from the viewpoints of improving the diffusion of sulfur-containing compounds in the fatty acid ester into the interior of the catalyst and the diffusion of hydrogenolyzed products of the sulfur-containing compounds from the interior of the catalyst, and thereby improving the catalytic activity, and of maintaining the catalytic activity, based on the total pore volume, 50% or more, preferably 60% or more, more preferably 70% or more, further preferably 75% or more, furthermore preferably 80% or more, furthermore preferably 83% or more, and furthermore preferably 88% or more and, from the viewpoints of improving the efficiency of contact between the catalyst metal and sulfur-containing compounds in the interior of the catalyst, and thereby improving the catalytic activity, based on the total pore volume, preferably 100% or less, more preferably 97% or less, further preferably 96% or less, furthermore preferably 95% or less, and furthermore preferably 90% or less.

The mode of the pore size of the catalyst used in the present invention is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 0.1 μm or more, more preferably 1 μm or more, further preferably 10 μm or more, furthermore preferably 15 μm or more, furthermore preferably 19 μm or more, and furthermore preferably 21 μm or more and, from the viewpoints of improving the efficiency of contact between the catalyst metal and sulfur-containing compounds in the interior of the catalyst, and thereby improving the catalytic activity, and of improving the strength of the catalyst, preferably 100 μm or less, more preferably 85 μm or less, further preferably 70 μm or less, furthermore preferably 61 μm or less, furthermore preferably 52 μm or less, furthermore preferably 40 μm or less, furthermore preferably 30 μm or less, and furthermore preferably 25 μm or less.

The median of the pore size of the catalyst used in the present invention is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 0.1 μm or more, more preferably 1 μm or more, further preferably 6 μm or more, furthermore preferably 10 μm or more, and furthermore preferably 15 μm or more and, from the viewpoints of improving the efficiency of contact between the catalyst metal and sulfur-containing compounds in the interior of the catalyst, and thereby improving the catalytic activity, and of improving the strength of the catalyst, preferably 100 μm or less, more preferably 85 μm or less, further preferably 70 μm or less, furthermore preferably 65 μm or less, furthermore preferably 50 μm or less, furthermore preferably 35 μm or less, and furthermore preferably 25 μm or less.

The porosity of the catalyst used in the present invention is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 30% or more, more preferably 35% or more, further preferably 50% or more, furthermore preferably 55% or more, and furthermore preferably 60% or more and, from the viewpoints of improving the efficiency of contact between the catalyst metal and sulfur-containing compounds in the interior of the catalyst, and thereby improving the catalytic activity, and of improving the strength of the catalyst, preferably 99% or less, more preferably 90% or less, further preferably 80% or less, furthermore preferably 75% or less, furthermore preferably 70% or less, and furthermore preferably 65% or less.

The specific surface area of the catalyst used in the present invention is, from the viewpoints of improving the efficiency of contact between the catalyst metal and sulfur-containing compounds in the interior of the catalyst, and thereby improving the catalytic activity, preferably 0.1 $m^2/g$ or more, more preferably 0.8 $m^2/g$ or more, further preferably 10 $m^2/g$ or more, furthermore preferably 15 $m^2/g$ or more, furthermore preferably 20 $m^2/g$ or more, furthermore preferably 25 $m^2/g$ or more, furthermore preferably 30 $m^2/g$ or more, and furthermore preferably 35 $m^2/g$ or more and, from the viewpoint of improving the strength of the catalyst, preferably 500 $m^2/g$ or less, more preferably 250 $m^2/g$ or less, further preferably 100 $m^2/g$ or less, furthermore preferably 60 $m^2/g$ or less, and furthermore preferably 40 $m^2/g$ or less.

The bulk density of the catalyst used in the present invention is, from the viewpoint of improving the strength of the catalyst, and from the viewpoint of increasing the amount of the catalyst filling the reactor, preferably 100 $kg/m^3$ or more, more preferably 200 $kg/m^3$ or more, further preferably 300 $kg/m^3$ or more, furthermore preferably 350 $kg/m^3$ or more, furthermore preferably 400 $kg/m^3$ or more, and furthermore preferably 450 $kg/m^3$ or more and, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and from the viewpoint of reducing the pressure loss caused when raw reaction materials or reaction products pass through the interior of the catalyst, preferably 10,000 $kg/m^3$ or less, more preferably 2,500 $kg/m^3$ or less, further preferably 2,000 $kg/m^3$ or less, furthermore preferably 1,000 $kg/m^3$ or less, furthermore preferably 770 $kg/m^3$ or less, furthermore preferably 700 $kg/m^3$ or less, and furthermore preferably 500 $kg/m^3$ or less.

The volume of pores with a pore diameter of 0.02 μm or more and 0.2 μm or less in the catalyst used in the present invention is, from the viewpoints of improving the efficiency of contact between the catalyst metal and sulfur-containing compounds in the interior of the catalyst, and thereby improving the catalytic activity, preferably 0.005 mL/g or more, more preferably 0.01 mL/g or more, and further preferably 0.05 mL/g or more and, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 0.14 mL/g or less, more preferably 0.12 mL/g or less, and further preferably 0.10 mL/g or less.

The total pore volume of the catalyst used in the present invention, the volume of pores with a pore diameter of 0.1 μm or more and 500 μm or less, the mode and the median of the pore size, the porosity, the specific surface area, the bulk density and the volume of pores with a pore diameter of 0.02 μm or more and 0.2 μm or less can be measured by the methods described in the Examples.

The shape of the catalyst may be any of a sphere, a cylinder, a sheet, a tube, a honeycomb, an unfixed shape and the like, but a sheet is preferable because it is easy to process the catalyst into a shape suitable for use.

When the catalyst is a sheet, the catalyst may be a long band, and for example, a sheet wound into a roll may also be used. When the catalyst is a sheet, the thickness is, from the viewpoint of improving the strength of the catalyst, preferably 0.1 mm or more, more preferably 0.5 mm or more, and further preferably 0.8 mm or more and, from the viewpoints of reducing the diffusion distances of sulfur-containing compounds and hydrogenolyzed products of the sulfur-containing compounds, and thereby improving the catalytic activity, and from the viewpoint of maintaining the catalytic activity, preferably 10 mm or less, more preferably 2 mm or less, and further preferably 1.2 mm or less.

The amount of the catalyst metal carried per unit mass of the catalyst used in the present invention is, from the viewpoints of improving the efficiency of contact between the catalyst metal and sulfur compounds in the interior of the catalyst, and thereby improving the catalytic activity, preferably 0.01 g/g or more, more preferably 0.1 g/g or more, further preferably 0.15 g/g or more, furthermore preferably 0.2 g/g or more, furthermore preferably 0.25 g/g or more, and furthermore preferably 0.27 g/g or more and, from the viewpoint of improving the catalytic activity per mass of the catalyst metal, preferably 0.7 g/g or less, more preferably 0.5 g/g or less, further preferably 0.4 g/g or less, furthermore preferably 0.35 g/g or less, furthermore preferably 0.33 g/g or less, and furthermore preferably 0.29 g/g or less.

The amount of the catalyst metal carried per unit volume of the catalyst used in the present invention is, from the viewpoints of improving the efficiency of contact between the catalyst metal and sulfur compounds in the interior of the catalyst, and thereby improving the catalytic activity, preferably 0.02 g/mL or more, more preferably 0.03 g/mL or more, further preferably 0.05 g/mL or more, and furthermore preferably 0.1 g/mL or more and, from the viewpoint of improving the catalytic activity per mass of the catalyst metal, preferably 1.0 g/mL or less, more preferably 0.8 g/mL or less, further preferably 0.6 g/mL or less, furthermore preferably 0.4 g/mL or less, furthermore preferably 0.3 g/mL or less, and furthermore preferably 0.2 g/mL or less.

[Catalyst Metal]

The catalyst used in the present invention contains as the catalyst metal one or more elements selected from the elements of group 9, group 10 and group 11 of the periodic table. The element(s) selected from the elements of group 9, group 10 and group 11 of the periodic table is, from the viewpoint of improving the catalytic activity, preferably Co, Ni or Cu, and more preferably Ni. Also, the catalyst used in the present invention may contain an element other than the element(s) selected from the elements of group 9, group 10 and group 11 of the periodic table. When the catalyst used in the present invention contains an element other than the element(s) selected from the elements of group 9, group 10 and group 11 of the periodic table, the atomic ratio of the element to the catalyst metal is, from the viewpoint of improving the catalytic activity, preferably 1/20 or more, more preferably 1/15 or more, and further preferably 1/10 or more and, from the same viewpoint, preferably 1/1 or less, more preferably 1/5 or less, and further preferably 1/7 or less.

The element other than the element (s) selected from the elements of group 9, group 10 and group 11 of the periodic table is not specifically restricted, but examples thereof include an alkaline earth metal, and from the viewpoint of improving the catalytic activity, the element is preferably Mg or Ca, and more preferably Mg.

From the viewpoint of handling, the catalyst metal preferably exists as a catalyst metal compound in the catalyst of the present invention, and from the same viewpoint, the catalyst metal compound preferably exists as an oxide.

[Support of Catalyst]

A porous structure is preferably used as the support of the catalyst used in the production method of the present invention, from the viewpoints of improving the diffusion of sulfur-containing compounds into the interior of the catalyst, the diffusion of hydrogenolyzed products of the sulfur-containing compounds from the interior of the catalyst and the efficiency of contact between the catalyst metal and sulfur-containing compounds in the interior of the catalyst, and thereby improving the catalytic activity, and of maintaining the catalytic activity.

From the viewpoint of heat resistance, the constituent material of the porous structure is preferably a metal such as Al, Ni, Cu, Ti, Fe and Co, an alloy such as Al alloy, Ti alloy and stainless or ceramics such as silica, alumina, silica-alumina, calcia-magnesia-silica, titania, zirconia, silicon carbide, mullite, cordierite, silicon nitride, aluminum nitride, barium titanate, zinc oxide, calcium oxide and magnesium oxide, and more preferably ceramics.

From the viewpoints of improving the diffusion of sulfur-containing compounds into the interior of the catalyst, the diffusion of hydrogenolyzed products of the sulfur-containing compounds from the interior of the catalyst and the efficiency of contact between the catalyst metal and sulfur-containing compounds in the interior of the catalyst, and thereby improving the catalytic activity, and of maintaining the catalytic activity, the ceramics are silica, alumina, silica-alumina, calcia-magnesia-silica, titania or zirconia, further preferably silica, alumina, silica-alumina or calcia-magnesia-silica, and furthermore preferably silica-alumina or calcia-magnesia-silica.

The total pore volume of the porous structure is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 0.1 mL/g or more, more preferably 0.15 mL/g or more, further preferably 0.6 mL/g or more, furthermore preferably 0.9 mL/g or more, furthermore preferably 1 mL/g or more, furthermore preferably 1.1 mL/g or more, furthermore preferably 1.2 mL/g or more, furthermore preferably 2 mL/g or more, furthermore preferably 3 mL/g or more, and furthermore preferably 3.5 mL/g or more and, from the viewpoints of improving the efficiency of contact between the catalyst metal and sulfur-containing compounds in the interior of the catalyst, and thereby improving the catalytic activity, and from the viewpoint of improving the strength of the catalyst, preferably 10 mL/g or less, more preferably 7.5 mL/g or less, further preferably 7 mL/g or less, and furthermore preferably 5 mL/g or less.

The volume of pores with a pore size of 0.1 μm or more and 500 μm or less in the porous structure is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, based on the total pore volume, preferably 50% or more, more preferably 80% or more, further preferably 90% or more, and further preferably 95% or more and, from the viewpoints of improving the efficiency of contact between the catalyst metal and sulfur-containing compounds in the interior of the catalyst, and thereby improving the catalytic activity, preferably 100% or less.

The mode of the pore size of the porous structure is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 0.1 μm or more, more preferably 1 μm or more, further preferably 10 μm or more, and furthermore preferably 20 μm or more and, from the viewpoints of improving the efficiency of contact between the catalyst metal and sulfur-containing compounds in the interior of the catalyst, and thereby improving the catalytic activity, and of improving the strength of the catalyst, preferably 500 μm or less, more preferably 200 μm or less, further preferably 100 μm or less, and furthermore preferably 60 μm or less.

The median of the pore size of the porous structure is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 0.1 μm or more, more preferably 1 μm or more, further preferably 10 μm or more, and furthermore preferably 20 μm or more and, from the viewpoints of improving the efficiency of contact between the catalyst metal and sulfur-containing compounds in the interior of the catalyst, and thereby improving the catalytic activity, and of improving the strength of the catalyst, preferably 500 μm or less, more preferably 200 μm or less, further preferably 140 μm or less, furthermore preferably 100 μm or less, and furthermore preferably 60 μm or less.

The porosity of the porous structure is, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity, preferably 30% or more, more preferably 40% or more, further preferably 50% or more, furthermore preferably 55% or more, furthermore preferably 60% or more, and furthermore preferably 70% or more and, from the viewpoints of improving the efficiency of contact between the catalyst metal and sulfur-containing compounds in the interior of the catalyst, and thereby improving the catalytic activity, and of improving the strength of the catalyst, preferably 99% or less, more preferably 95% or less, and further preferably 93% or less.

The bulk density of the porous structure is, from the viewpoint of improving the strength of the catalyst, and from the viewpoint of increasing the amount of the catalyst filling the reactor, preferably 10 kg/m$^3$ or more, more preferably 100 kg/m$^3$ or more, and further preferably 150 kg/m$^3$ or more and, from the viewpoints of improving the diffusion of sulfur-containing compounds into the interior of the catalyst, and thereby improving the catalytic activity, and from the viewpoint of reducing the pressure loss caused when raw reaction materials or reaction products pass through the interior of the catalyst, preferably 7,000 kg/m$^3$ or less, more preferably 4,000 kg/m$^3$ or less, further preferably 2,400 kg/m$^3$ or less, furthermore preferably 1,000 kg/m$^3$ or less, furthermore preferably 500 kg/m$^3$ or less, furthermore preferably 300 kg/m$^3$ or less, and furthermore preferably 250 kg/m$^3$ or less.

The total pore volume of the porous structure, the volume of pores with a pore diameter of 0.1 μm or more and 500 μm or less, the mode and the median of the pore size, the porosity, the specific surface area and the bulk density can be measured by the methods described in the Examples.

The porous structure is preferably a fiber structure or a porous compact from the viewpoint of increasing the amount of the catalyst metal to be carried, and from the viewpoint of improving the strength of the catalyst, and the porous structure is more preferably a fiber structure from the viewpoint of increasing the amount of the catalyst metal to be carried, and from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and of maintaining the catalytic activity.

The fiber structure used in the present invention is aggregated fibers. From the viewpoints of carrying the catalyst and of easiness in processing the catalyst, the fiber structure is preferably woven fabric, knitted fabric or a nonwoven cloth, and more preferably a nonwoven cloth. When the fiber structure is used, the shape of the fiber structure is, from the viewpoint of workability, preferably a sheet, a tube, a honeycomb or an unfixed shape, and from the viewpoint of easiness in processing the obtained catalyst into a shape according to the use, more preferably a sheet. In addition, from the viewpoint of improving the productivity of the fiber structure, the fiber structure is preferably produced by a wet papermaking method or a dry papermaking method.

When a fiber structure sheet is used as the support, the thickness of the fiber structure is, from the viewpoint of improving the strength of the catalyst, preferably 0.1 mm or more, more preferably 0.5 mm or more, and further preferably 0.8 mm or more and, from the viewpoints of reducing the diffusion distances of sulfur-containing compounds and hydrogenolyzed products of the sulfur-containing compounds in the interior of the catalyst, thereby improving the diffusion of the sulfur compounds into the interior of the catalyst and the diffusion of the hydrogenolyzed products of the sulfur-containing compounds from the interior of the catalyst, and thereby improving the catalytic activity, and of maintaining the catalytic activity, preferably 10 mm or less, more preferably 5 mm or less, further preferably 2 mm or less, and furthermore preferably 1.2 mm or less.

The aspect ratio of the fibers of the fiber structure (the ratio of the fiber length to the diameter of the cross section of the fibers) is, from the viewpoint of increasing the amount of the catalyst metal to be carried, preferably five or more, more preferably 10 or more, and further preferably 20 or more and, from the viewpoints of maintaining the shape of the fiber structure and maintaining the catalytic activity, preferably 100,000 or less, more preferably 10,000 or less, further preferably 5,000 or less, and furthermore preferably 1,000 or less.

The mean diameter of the fibers is, from the viewpoints of maintaining the shape of the fiber structure and maintaining the catalytic activity, preferably 100 nm or more, more preferably 200 nm or more, further preferably 500 nm or more, and furthermore preferably 1,000 nm or more and, from the viewpoint of increasing the amount of the catalyst metal to be carried, preferably 50,000 nm or less, more preferably 30,000 nm or less, and further preferably 10,000 nm or less.

The mean length of the fibers is, from the viewpoint of increasing the amount of the catalyst metal to be carried, preferably 0.5 μm or more, more preferably 5 μm or more, further preferably 20 μm or more, and furthermore preferably 60 μm or more and, from the viewpoint of availability, preferably 500,000 μm or less, more preferably 50,000 μm or less, further preferably 30,000 μm or less, and furthermore preferably 10,000 μm or less.

From the viewpoint of heat resistance, the fibers are preferably made of a combination of one or two or more kinds of fiber selected from ceramic fibers and metal fibers, and more preferably ceramic fibers. From the viewpoints of heat resistance and availability, the ceramic fibers are preferably silica fibers, alumina fibers, silica-alumina fibers, calcia-magnesia-silica fibers, titania fibers or zirconia fibers, and more preferably silica-alumina fibers or calcia-magnesia-silica fibers. From the viewpoint of improving the productivity, the fibers are preferably produced by a spinning method or a blowing method.

The porous compact used in the present invention is a compact obtained by molding particles of a metal, an alloy or ceramics and then fusion bonding the particles by heating or the like. The particles constituting the compact are fusion bonded to each other in the compact to form a strong network, and due to this network, the compact carries the catalyst metal and has enough space for the diffusion of raw reaction materials and reaction products. In addition, its external size is suitable for the catalyst used in fixed bed reaction process.

When a porous compact is used as the porous structure in the present invention, the porous compact may have an unfixed shape or a shape such as a sphere or a cylinder, but from the viewpoint of the amount of the catalyst which fills the reactor, the shape is preferably a sphere or a cylinder, and more preferably a sphere.

When a spherical porous compact is used as the porous structure, the outer diameter is, from the viewpoint of using for a catalyst used in fixed bed reaction process, and from the viewpoint of reducing the pressure loss caused when raw reaction materials or reaction products pass through the catalyst-filled layer, preferably 0.1 mm or more, more preferably 0.5 mm or more, further preferably 1 mm or more, and furthermore preferably 4 mm or more and, from the viewpoint of increasing the amount of the catalyst filling the reactor, preferably 100 mm or less, more preferably 50 mm or less, further preferably 10 mm or less, and furthermore preferably 6 mm or less.

From the viewpoints of heat resistance and availability, the porous compact is preferably ceramics such as silica, alumina, alumina-silica, titania or zirconia.

[Production Method of Catalyst]

From the viewpoint of increasing the amount of the catalyst metal to be carried, the method for producing the catalyst used in the present invention is preferably a method in which a catalyst precursor or a catalyst metal oxide is carried on a support and then calcined. The catalyst precursor used herein is a compound which is converted to a catalyst metal oxide by calcining.

Exemplary methods for carrying a catalyst precursor or a catalyst metal oxide on a support include an impregnation method, a co-precipitation method, a homogeneous mixing method or the like. Among them, from the viewpoint of increasing the amount of the catalyst metal to be carried, and from the viewpoints of improving the efficiency of contact between the catalyst metal and sulfur-containing compounds in the interior of the catalyst, and thereby improving the catalytic activity, the method is preferably an impregnation method, namely an impregnation method by immersing a support in a slurry containing a catalyst precursor or a catalyst metal oxide. In this regard, the slurry containing a catalyst precursor and the slurry containing a catalyst metal oxide are also called a catalyst precursor coating material and a catalyst metal oxide coating material, respectively. In this case, the step of preparing a coating material of a catalyst precursor or a catalyst metal oxide, the carrying step and the calcining step are conducted in this order in the production step of the catalyst.

(Coating Material Preparation Step)

The coating material preparation step is a step in which a catalyst precursor coating material or a catalyst metal oxide coating material is produced by dispersing a catalyst precursor or a catalyst metal oxide in a dispersion medium.

From the viewpoint of improving the catalytic activity, and from the viewpoint of the availability of raw materials, the catalyst precursor is preferably a solution of a compound containing the same element as the catalyst metal, more preferably a solution of a salt of the same element as the catalyst metal and a strong acid or of an ammine complex of the same element as the catalyst metal, and further preferably a catalyst precursor precipitated by adding an alkali agent to a solution of a salt of the same element as the catalyst metal and a strong acid. Here, the strong acid is an inorganic acid with an acid dissociation constant pKa in an aqueous solution at 25° C. of less than 0 or sulfuric acid. From the viewpoint of improving the catalytic activity, and from the viewpoint of availability of raw materials, the salt of the same element as the catalyst metal and the strong acid is preferably nitrate or sulfate. From the viewpoint of improving the catalytic activity, the precipitated catalyst precursor is preferably dispersed in a dispersion medium to prepare a slurry, after filtration through a filter, separation from the liquid phase by a method such as centrifugation, washing with water such as deionized water, drying or the like.

The alkali agent used for precipitating the catalyst precursor is, from the viewpoint of improving the catalytic activity, and from the viewpoint of availability, preferably hydroxide or carbonate of an alkali metal, more preferably carbonate of an alkali metal, and from the viewpoint of improving the catalytic activity, further preferably sodium carbonate. From the viewpoint of workability in precipitating the catalyst precursor, the alkali agent is preferably used as a solution.

From the viewpoint of improving the catalytic activity, and from the viewpoint of availability, the solvent used for precipitating the catalyst precursor is preferably one or more kinds selected from water and hydrophilic solvents, more preferably one or more kinds selected from water and alcohols having one or more and three or less carbon atoms, further preferably one or more kinds selected from water, methanol, ethanol and isopropanol, furthermore preferably one or more kinds selected from water and isopropanol, and furthermore preferably water. The solvents used for the solution of the salt of the raw material of the catalyst precursor and the strong acid and the solution of the alkali agent are the same as those in the embodiments of the solvent used for precipitating the catalyst precursor.

Moreover, a catalyst metal oxide can be produced by calcining the obtained catalyst precursor before the catalyst precursor is carried on a support. This step is called a preliminary calcining step. The temperature of the preliminary calcining is, from the viewpoint of improving the catalytic activity, preferably 300° C. or higher, and more preferably 350° C. or higher and, from the same viewpoint, preferably 800° C. or lower, more preferably 600° C. or lower, and further preferably 450° C. or lower. The period of the preliminary calcining is, from the viewpoint of improving the catalytic activity, preferably two hours or longer, and more preferably three hours or longer and, from the viewpoint of improving the productivity, preferably 10 hours or shorter, and more preferably five hours or shorter.

From the viewpoint of carrying the catalyst precursor or the catalyst metal oxide easily on the porous structure, the dispersion medium of the catalyst precursor coating material or the catalyst metal oxide coating material is preferably one or more kinds selected from water and hydrophilic solvents, more preferably one or more kinds selected from water and alcohols having one or more and three or less carbon atoms, further preferably one or more kinds selected from water, methanol, ethanol and isopropanol, and furthermore preferably one or more kinds selected from water and isopropanol. The catalyst precursor coating material or the catalyst metal oxide coating material may contain a dispersing agent. The dispersing agent is a polymeric dispersing agent, a surfactant-type dispersing agent or an inorganic dispersing agent, and from the viewpoint of improving the dispersibility of the particles of the catalyst precursor or the catalyst metal oxide in the catalyst precursor coating material or the catalyst metal coating material, a polymeric dispersing agent is preferable.

From the viewpoints of binding the catalyst metal oxide and the porous structure in the calcining step and increasing the amount of the catalyst metal to be carried, the coating material preferably contains a binder. From the viewpoint of increasing the amount of the catalyst metal to be carried, and from the viewpoint of maintaining the catalytic activity, the binder is preferably an oxide of a metal other than the catalyst metal, more preferably one or more kinds selected from the group consisting of aluminum oxide, silicon oxide, antimony oxide, titanium oxide, zirconium oxide, magnesium oxide and calcium oxide, further preferably one or more kinds selected from aluminum oxide, magnesium oxide and silicon oxide, furthermore preferably one or more kinds selected from silicon oxide and aluminum oxide, and furthermore preferably silicon oxide.

From the viewpoint of increasing the amount of the catalyst metal to be carried, the binder is added to the catalyst precursor coating material or the catalyst metal oxide coating material, preferably as a powder of the binder, a sol of the binder or a slurry prepared by dispersing the binder in a solvent, and more preferably as a powder of the binder or a sol of the binder.

The concentration of the catalyst precursor or the catalyst metal oxide in the catalyst precursor coating material or the catalyst metal oxide coating material is, from the viewpoint of increasing the amount of the catalyst metal to be carried, preferably 1% by mass or more, more preferably 5% by mass or more, further preferably 15% by mass or more, and furthermore preferably 20% by mass or more and, from the viewpoint of improving the dispersibility of the catalyst precursor or the catalyst metal oxide, preferably 40% by mass or less, more preferably 30% by mass or less, and further preferably 28% by mass or less.

The binder content in the coating material is, from the viewpoint of increasing the amount of the catalyst metal to be carried, and from the viewpoint of maintaining the catalytic activity, based on the catalyst precursor or the catalyst metal oxide, preferably 1% by mass or more, more preferably 5% by mass or more, further preferably 10% by mass or more, furthermore preferably 15% by mass or more, furthermore preferably 20% by mass or more, and furthermore preferably 23% by mass or more and, from the viewpoint of increasing the amount of the catalyst metal to be carried, preferably 30% by mass or less, and more preferably 27% by mass or less.

The mean particle size of the catalyst precursor or the catalyst metal oxide in the coating material is, from the viewpoint of increasing the amount of the catalyst metal to be carried, and from the viewpoint of improving the dispersibility of the catalyst precursor or the catalyst metal oxide in the coating material, preferably 100 μm or less, more preferably 10 μm or less, further preferably 7 μm or less, furthermore preferably 2 μm or less, furthermore preferably 1.2 μm or less, and furthermore preferably 0.7 μm or less and, from the viewpoints of improving the productivity of the catalyst precursor coating material or the catalyst metal oxide coating material and the dispersibility of the catalyst precursor or the catalyst metal oxide, preferably 0.1 μm or more, more preferably 0.2 μm or more, and further preferably 0.3 μm or more. The mean particle size of the catalyst precursor or the catalyst metal oxide can be adjusted to the above value by wet dispersion or the like. The mean particle size of the catalyst precursor or the catalyst metal oxide in the catalyst precursor coating material or the catalyst metal oxide coating material can be measured by the method described in the Examples.

In the coating material preparation step, the necessary components can be mixed in one stage using a media mill or a paint shaker to form a coating material, but it is preferable to form a coating material in two mixing stages of preliminary mixing and subsequent main mixing. It is preferable to produce a catalyst precursor coating material or a catalyst metal oxide coating material with a small particle size in two mixing stages of preliminary mixing and main mixing as described above, because the catalyst precursor coating material or the catalyst metal oxide coating material easily enters the spaces in the porous structure in the carrying step which is conducted next. In addition, a mixing method using a non-media disperser can also be applied.

(Carrying Step)

The carrying step is a step in which the catalyst precursor coating material or the catalyst metal oxide coating material obtained in the coating material preparation step is carried on a support. As the method for carrying the catalyst precursor coating material or the catalyst metal oxide coating material on a support, from the viewpoints of uniformly carrying the catalyst precursor or catalyst metal oxide coating material and increasing the carried amount per volume, a method in which the catalyst precursor coating material or the catalyst metal oxide coating material is brought into contact with the support or a method in which an external force is applied to the catalyst precursor coating material or the catalyst metal oxide coating material which is in contact with the support can be preferably applied. As the method for bringing the catalyst precursor coating material or the catalyst metal oxide coating material into contact with the support, a method in which the support is immersed in the catalyst precursor coating material or the catalyst metal oxide coating material can be applied. As the method for applying an external force, a method using a roller or a method of applying ultrasonic vibrations can be applied.

After the carrying step, a step of removing excess catalyst precursor coating material or catalyst metal oxide coating material can be conducted if necessary. By conducting this step, the removal rate of the catalyst precursor or the catalyst metal oxide in the shaping step described below can be decreased.

The support from which the excess catalyst precursor coating material or catalyst metal oxide coating material has been removed is dried if necessary. The drying may be heat drying or natural drying, but from the viewpoint of improving the productivity, heat drying is preferable, and a method of heat drying at a temperature same as or higher than the boiling point of the solvent used in the coating material preparation step is preferable. In this case, the support can be compressed at the same time to control the pores of the catalyst. That is, in the drying step, spaces, namely pores, generate in the support when the solvent is evaporated and removed by drying, resulting in a high porosity, and the pore size and the pore volume can be adjusted by controlling the pores by compression.

The specific temperature of the drying is, from the viewpoints of sufficiently removing the solvent and improving the catalytic activity, preferably 30° C. or higher, more preferably 80° C. or higher, and further preferably 100° C. or higher and, from the viewpoints of reducing the facility load and energy consumption, preferably 150° C. or lower, and more preferably 140° C. or lower. In addition, the period of the drying is, from the viewpoints of sufficiently removing the solvent and improving the catalytic activity, preferably 0.1 hours or longer, and more preferably 0.5 hours or longer and, from the viewpoint of improving the catalytic activity, and from the viewpoint of improving the productivity, preferably 24 hours or shorter, more preferably five hours or shorter, and further preferably two hours or shorter.

(Calcining Step)

The calcining step is a step in which the catalyst precursor or the catalyst metal oxide carried on the support in the carrying step is calcined. In this step, the catalyst metal oxide binds to the support through the binder or directly. Moreover, when a catalyst precursor coating material is used in the carrying step, the catalyst precursor is converted to a catalyst metal oxide, and the generated catalyst metal oxide binds to the support through the binder or directly.

The temperature of the calcining is, from the viewpoints of converting the catalyst precursor to a catalyst metal oxide, binding the catalyst metal oxide to the support and improving the catalytic activity, preferably 300° C. or higher, and more preferably 350° C. or higher, and preferably 800° C. or lower, more preferably 600° C. or lower, and further preferably 450° C. or lower. Moreover, the period of the calcining is, from the viewpoints of converting the catalyst precursor to a catalyst metal oxide, binding the catalyst metal oxide to the support and improving the catalytic activity, preferably 0.1 hours or longer, and more preferably two hours or longer and, from the viewpoint of improving the productivity, preferably 24 hours or shorter, more preferably 10 hours or shorter, and further preferably five hours or shorter. The calcining step is preferably conducted in air atmosphere at atmospheric pressure.

After drying in the carrying step or after the calcining step, a shaping step for processing the shape may be conducted depending on the kind of support such as a fiber structure. Through the shaping step, the shape of the catalyst can be changed according to the use. Shaping includes cutting, deformation and the like, and the shape can be changed into a honeycomb, a cylinder, a multilayer roll of a sheet or the like.

The carried amount of the catalyst metal oxide and the binder per unit volume of the catalyst is, from the viewpoints of improving the efficiency of contact between the catalyst metal and sulfur compounds in the interior of the catalyst, and thereby improving the catalytic activity, preferably 0.05 g/mL or more, more preferably 0.06 g/mL or more, further preferably 0.1 g/mL or more, furthermore preferably 0.15 g/mL or more, furthermore preferably 0.2 g/mL or more, and furthermore preferably 0.25 g/mL or more and, from the viewpoint of improving the catalytic activity per mass of the catalyst metal, from the viewpoints of improving the diffusion of sulfur-containing compounds into the interior of the catalyst and the diffusion of hydrogenolyzed products of the sulfur-containing compounds from the interior of the catalyst, and thereby improving the catalytic activity, and from the viewpoint of reducing the pressure loss caused when raw reaction materials or reaction products pass through the interior of the catalyst, preferably 2 g/mL or less, more preferably 1.0 g/mL or less, further preferably 0.8 g/mL or less, furthermore preferably 0.7 g/mL or less, furthermore preferably 0.5 g/mL or less, further preferably 0.4 g/mL or less, and furthermore preferably 0.3 g/mL or less. The carried amount of the catalyst metal oxide and the binder per unit volume of the catalyst can be calculated by the method described in the Examples.

<Production Method of Fatty Acid Ester>

[Reduction of Catalyst]

From the viewpoint of improving the catalytic activity, the catalyst is preferably reduced before the reaction. The catalyst is activated by the reduction. From the viewpoint of improving the productivity, the reducing agent is preferably hydrogen, carbon monoxide, formaldehyde or the like, and more preferably hydrogen. When a reducing agent of a gas type is used, the reducing agent may be used alone, or the reducing agent may be mixed with an inert gas such as nitrogen or water vapor.

When hydrogen is used for the reduction, a gas phase system in which hydrogen gas is brought into contact with a dry catalyst may be used, and a liquid phase system in which the catalyst is immersed in a liquid and hydrogen is flown may be also used. As the liquid, hydrocarbon such as liquid paraffin, an aliphatic alcohol, an aliphatic ester, carboxylic acid or the like can be used.

When hydrogen is used as the reducing agent and when the catalyst is reduced and activated in a gas phase system, from the viewpoint of improving the catalytic activity, the reduction is conducted in hydrogen flow preferably at 300° C. or higher, and more preferably at 400° C. or higher, and the reduction is conducted preferably at 800° C. or lower, more preferably at 600° C. or lower, and further preferably at 500° C. or lower. Hydrogen used here may be 100% hydrogen or may be diluted with an inert gas. Diluted hydrogen is preferable to prevent heat generation due to rapid reduction, and the concentration of diluted hydrogen is, from the viewpoint of improving the productivity, preferably 0.1% by volume or more, more preferably 1% by volume or more, and further preferably 3% by volume or more and, from the viewpoint of reducing the facility load, preferably 10% by volume or less, and more preferably 5% by volume or less. The reduction is desirably conducted until the absorption of hydrogen stops. Specifically, from the viewpoint of improving the catalytic activity, the period of the reduction is preferably 0.1 hours or longer, more preferably one hour or longer, and further preferably four hours or longer and, from the viewpoint of improving the productivity, preferably 24 hours or shorter, more preferably 12 hours or shorter, and further preferably six hours or shorter.

The catalyst which has been reduced and activated may react strongly with oxygen in the air and generate heat when the catalyst is left in the air as it is. Thus, it is preferable to form an oxide film over the surface of the catalyst metal which has been reduced and activated to stabilize the catalyst. From the viewpoint of stabilizing the catalyst metal which has been reduced and activated, the oxidation stabilization is conducted in a flow of an inert gas, such as nitrogen, containing oxygen in an amount of preferably 0.1% by volume or more, and more preferably 0.5% by volume or more, and preferably 5% by volume or less, and more preferably 1.5% by volume or less. From the same viewpoint, the temperature of the oxidation stabilization is preferably 0° C. or higher, and more preferably 20° C. or higher, and preferably 200° C. or lower, more preferably 100° C. or lower, and further preferably 50° C. or lower. The period of the oxidation stabilization is, from the same viewpoint, preferably one hour or longer, more preferably five hours or longer, and further preferably seven hours or longer and, from the viewpoint of improving the productivity, preferably 24 hours or shorter, more preferably 12 hours or shorter, and further preferably nine hours or shorter.

When hydrogen is used as the reducing agent and when the catalyst is reduced and activated in a liquid phase system, from the viewpoint of improving the catalytic activity, the reduction is conducted in hydrogen flow preferably at 100° C. or higher, and more preferably at 150° C. or higher, and the reduction is conducted preferably at 300° C. or lower, and more preferably at 200° C. or lower. The hydrogen concentration of hydrogen used is preferably 100% by volume from the viewpoint of improving the catalytic activity. Hydrogen diluted with the inert gas can be used to prevent heat generation due to rapid reduction. The hydrogen concentration in this case is, from the viewpoint of improving the catalytic activity, preferably 0.1% by volume or more, more preferably 1% by volume or more, further preferably 10% by volume or more, furthermore preferably 30% by volume or more, furthermore preferably 50% by volume or more, furthermore preferably 70% by volume or more, and furthermore preferably 90% by volume or more. The reduction is desirably conducted until the absorption of hydrogen stops. Specifically, from the viewpoint of improving the catalytic activity, the period of the reduction is preferably 0.1 hours or longer, and more preferably one hour or longer and, from the viewpoint of improving the productivity, preferably 48 hours or shorter, and more preferably 24 hours or shorter.

It is preferable to subject the catalyst which has been reduced and activated directly to the reaction from the viewpoint of production efficiency.

[Desulfurization]

The method for producing a fatty acid ester of the present invention is a method for producing a fatty acid ester with a low sulfur concentration by subjecting the fatty acid ester to desulfurization for sulfur-containing compounds therein using the catalyst.

Distillation can be conducted before or after the desulfurization for the purpose of removing other impurities and further removing sulfur compounds. In addition, when oil is used as the fatty acid ester, gum substances and the like are preferably removed before the desulfurization from the viewpoint of improving the productivity.

The process of the desulfurization is a continuous, batch or semi-batch process, and preferably a continuous process from the viewpoint of improving the productivity. The apparatus for conducting the desulfurization is a tubular apparatus filled with the catalyst or a tank apparatus filled with the catalyst, and preferably a tubular apparatus filled with the catalyst from the viewpoint of improving the productivity. From the viewpoint of improving the productivity, the desulfurization is preferably conducted by a continuous process by passing a fatty acid ester liquid through a tubular apparatus filled with the catalyst. The continuous reaction process by passing the fatty acid ester liquid through a tubular apparatus filled with the catalyst is also called fixed bed reaction process.

When the desulfurization is conducted, the ambient gas is preferably hydrogen, and an inert gas may be mixed. The inert gas is nitrogen, argon, helium or methane.

When the desulfurization is conducted, the ambient pressure as gauge pressure is, from the viewpoint of removing sulfur-containing compounds, preferably 0.01 MPa or higher, more preferably 0.1 MPa or higher, and further preferably 1 MPa or higher and, from the viewpoint of reducing the facility load, preferably 50 MPa or lower, more preferably 40 MPa or lower, and further preferably 30 MPa or lower.

The temperature of the desulfurization step is, from the viewpoint of removing sulfur-containing compounds, preferably 40° C. or higher, more preferably 50° C. or higher, and further preferably 110° C. or higher and, from the viewpoint of preventing the decomposition of the fatty acid ester, preferably 200° C. or lower, and more preferably 180° C. or lower.

When the desulfurization is conducted by a continuous process in a tubular apparatus, the liquid hourly space velocity (LHSV) of the fatty acid ester is, from the viewpoint of improving the productivity, preferably 0.01 [$Hr^{-1}$] or more, more preferably 0.1 [$Hr^{-1}$] or more, further preferably 1 [$Hr^{-1}$] or more, and furthermore preferably 4 [$Hr^{-1}$] or more and, from the viewpoint of removing sulfur-containing compounds, preferably 10 [$Hr^{-1}$] or less, more preferably 8 [$Hr^{-1}$] or less, and further preferably 6 [$Hr^{-1}$] or less.

When the desulfurization is conducted by a continuous process in a tubular apparatus and when hydrogen is used as the ambient gas, the flow rate of the ambient gas is, as the mole of hydrogen based on that of the ester group in the fatty acid ester which flows, from the viewpoint of removing sulfur-containing compounds, preferably one time or more, more preferably 10 times or more, and further preferably 20 times or more and, from the viewpoint of reducing the facility load, preferably 300 times or less, more preferably 100 times or less, and further preferably 30 times or less.

<Production Method of Alcohol>

The method for producing an alcohol of the present invention is a method in which hydrogenation is conducted using the fatty acid ester with a low sulfur content which is produced by the method of the present invention as the raw material. Specific embodiments of the conditions of the hydrogenation are described for example in JP-A-2007-224272.

As the alcohol production catalyst used for the hydrogenation of the fatty acid ester, generally known copper catalysts, noble metal catalysts such as palladium and platinum or the like are used. The copper catalysts are copper-chromium, copper-zinc, copper-iron-aluminum, copper-silica or the like. The hydrogenation can be conducted in the presence of any of the catalysts and by any reaction process which is generally used such as liquid phase suspension bed or fixed bed process.

When the reaction is conducted by a fixed bed reaction process, a catalyst which is shaped into a cylinder, pellets, a sphere or the like is used. From the viewpoint of reactivity, the reaction temperature is preferably 130° C. or higher, and more preferably 150° C. or higher, and preferably 300° C. or lower, and more preferably 270° C. or lower. From the viewpoint of reactivity, the reaction pressure as gauge pressure is preferably 0.1 MPa or higher and 30 MPa or lower. Considering the productivity and the reactivity, the LHSV is determined depending on the reaction condition.

As the alcohol production catalyst, usable is a catalyst having the same constitution as the catalyst used for the desulfurization of sulfur from the fatty acid ester, namely a catalyst which carries a catalyst metal on a support, contains as the catalyst metal one or more elements selected from the elements of group 9, group 10 and group 11 of the periodic table and has a total pore volume of 0.05 mL/g or more and in which the volume of pores with a pore size of 0.1 μm or more and 500 μm or less is 50% or more of the total pore volume of the catalyst.

In the foregoing description relating to the catalyst used for the desulfurization of sulfur from fatty acid esters, the phrases concerning improvements in the diffusion of sulfur-containing compounds into the interior of the catalyst, improvements in the diffusion of hydrogenolyzed products of the sulfur-containing compounds from the interior of the catalyst, and the resulting improvements in the catalytic activity may be understood, in the case of the alcohol production catalyst, through appropriate replacement with phrases concerning improvements in the diffusion of raw reaction materials into the interior of the catalyst, improvements in the diffusion of reaction products from the interior of the catalyst, and the resulting improvements in the selectivity. Likewise, in the foregoing description relating to the catalyst used for the desulfurization of sulfur from fatty acid esters, the phrases concerning improvements in the efficiency of contact between the catalyst metal and sulfur-containing compounds in the interior of the catalyst, and the resulting improvements in the catalytic activity may be understood, in the case of the alcohol production catalyst, through appropriate replacement with phrases concerning improvements in the efficiency of contact between the catalyst metal and raw reaction materials in the interior of the catalyst, and the resulting improvements in the catalytic activity.

The catalytic activity of the alcohol production catalyst means the rate of the hydrogenation for producing a corresponding alcohol from the fatty acid ester in the presence of the catalyst, and specifically, the catalytic activity can be represented by the decrease rate of the fatty acid ester content in the raw materials. Moreover, the selectivity of the alcohol production catalyst means the production amount of hydrocarbons in the hydrogenation, and specifically, the selectivity can be represented by the hydrocarbon content in the reaction solution at a certain point.

Among the catalysts having the same constitution as the catalyst used for the desulfurization of the fatty acid ester, from the viewpoints of improving the diffusion of raw reaction materials into the interior of the catalyst and the diffusion of reaction products from the interior of the catalyst, and thereby improving the selectivity, the alcohol production catalyst is preferably a catalyst which contains one or more elements selected from Co and Cu as the catalyst metal and has a total pore volume of 0.05 mL/g or more and in which the volume of pores with a pore size of 0.1 μm or more and 500 μm or less is 50% or more of the total pore volume. In particular, from the viewpoint of producing an alcohol from the fatty acid ester, the alcohol production catalyst preferably contains Cu as the catalyst metal.

Embodiments of the present invention are shown below.

<1>

A method for producing a fatty acid ester through desulfurization of sulfur from a fatty acid ester using a catalyst in which the catalyst carries a catalyst metal on a support, (a) the catalyst contains as the catalyst metal one or more elements selected from the elements of group 9, group 10 and group 11 of the periodic table, (b) the total pore volume of the catalyst is 0.05 mL/g or more, and (c) the volume of pores with a pore size of 0.1 μm or more and 500 μm or less is 50% or more of the total pore volume of the catalyst.

<2>

The method for producing a fatty acid ester described in <1> in which the total pore volume of the catalyst is preferably 0.15 mL/g or more, more preferably 0.5 mL/g or more, further preferably 0.7 mL/g or more, furthermore preferably 0.9 mL/g or more, and furthermore preferably 1 mL/g or more, and preferably 10 mL/g or less, preferably 4 mL/g or less, more preferably 2.5 mL/g or less, and further preferably 1.6 mL/g or less.

<3>

The method for producing a fatty acid ester described in <1> or <2> in which the volume of pores with a pore size of 0.1 μm or more and 500 μm or less in the catalyst is, based on the total pore volume, preferably 60% or more, more preferably 70% or more, further preferably 75% or more, furthermore preferably 80% or more, furthermore preferably 83% or more, and furthermore preferably 88% or more, and preferably 100% or less, more preferably 97% or less, further preferably 96% or less, furthermore preferably 95% or less, and furthermore preferably 90% or less.

<4>

The method for producing a fatty acid ester described in any one of <1> to <3> in which the mode of the pore size of the catalyst is preferably 0.1 μm or more, more preferably 1 μm or more, further preferably 10 μm or more, furthermore preferably 15 μm or more, furthermore preferably 19 μm or more, and furthermore preferably 21 μm or more, and preferably 100 μm or less, more preferably 85 μm or less, further preferably 70 μm or less, furthermore preferably 61 μm or less, furthermore preferably 52 μm or less, furthermore preferably 40 μm or less, furthermore preferably 30 μm or less, and furthermore preferably 25 μm or less.

<5>

The method for producing a fatty acid ester described in any one of <1> to <4> in which the median of the pore size of the catalyst is preferably 0.1 μm or more, more preferably 1 μm or more, further preferably 6 μm or more, furthermore preferably 10 μm or more, and furthermore preferably 15 μm or more, and preferably 100 μm or less, more preferably 85 μm or less, further preferably 70 μm or less, furthermore preferably 65 μm or less, furthermore preferably 50 μm or less, furthermore preferably 35 μm or less, and furthermore preferably 25 μm or less.

<6>

The method for producing a fatty acid ester described in any one of <1> to <5> in which the porosity of the catalyst is preferably 30% or more, more preferably 35% or more, further preferably 50% or more, furthermore preferably 55% or more, and furthermore preferably 60% or more, and preferably 99% or less, more preferably 90% or less, further preferably 80% or less, furthermore preferably 75% or less, furthermore preferably 70% or less, and furthermore preferably 65% or less.

<7>

The method for producing a fatty acid ester described in any one of <1> to <6> in which the specific surface area of the catalyst is preferably 0.1 m²/g or more, more preferably 0.8 m²/g or more, further preferably 10 m²/g or more, furthermore preferably 15 m²/g or more, furthermore preferably 20 m²/g or more, furthermore preferably 25 m²/g or more, furthermore preferably 30 m²/g or more, and furthermore preferably 35 m²/g or more, and preferably 500 m²/g or less, more preferably 250 m²/g or less, further preferably 100 m²/g or less, furthermore preferably 60 m²/g or less, and furthermore preferably 40 m²/g or less.

<8>

The method for producing a fatty acid ester described in any one of <1> to <7> in which the bulk density of the catalyst is preferably 100 kg/m³ or more, more preferably 200 kg/m³ or more, further preferably 300 kg/m³ or more, furthermore preferably 350 kg/m³ or more, furthermore preferably 400 kg/m³ or more, and furthermore preferably 450 kg/m³ or more, and preferably 10,000 kg/m³ or less, more preferably 2,500 kg/m³ or less, further preferably 2,000 kg/m³ or less, furthermore preferably 1,000 kg/m³ or less, furthermore preferably 770 kg/m³ or less, furthermore preferably 700 kg/m³ or less, and furthermore preferably 500 kg/m³ or less.

<9>

The method for producing a fatty acid ester described in any one of <1> to <8> in which the carried amount of the catalyst metal per unit mass of the catalyst is preferably 0.01 g/g or more, more preferably 0.1 g/g or more, further preferably 0.15 g/g or more, furthermore preferably 0.2 g/g or more, furthermore preferably 0.25 g/g or more, and furthermore preferably 0.27 g/g or more, and preferably 0.7 g/g or less, more preferably 0.5 g/g or less, further preferably 0.4 g/g or less, furthermore preferably 0.35 g/g or less, furthermore preferably 0.33 g/g or less, and furthermore preferably 0.29 g/g or less.

<10>

The method for producing a fatty acid ester described in any one of <1> to <9> in which the carried amount of the catalyst metal per unit volume of the catalyst is preferably 0.02 g/mL or more, more preferably 0.03 g/mL or more, further preferably 0.05 g/mL or more, and furthermore preferably 0.1 g/mL or more, and preferably 1.0 g/mL or less, more preferably 0.8 g/mL or less, further preferably 0.6 g/mL or less, furthermore preferably 0.4 g/mL or less, furthermore preferably 0.3 mL/g or less, and furthermore preferably 0.2 mL/g or less.

<11>

The method for producing a fatty acid ester described in any one of <1> to <10> in which the support of the catalyst has a porous structure.

<12>

The method for producing a fatty acid ester described in <11> in which the porous structure is made of preferably a metal, an alloy or ceramics, more preferably ceramics, further preferably silica, alumina, silica-alumina, calcia-magnesia-silica, titania or zirconia, further preferably silica, alumina, silica-alumina or calcia-magnesia-silica, and furthermore preferably silica-alumina or calcia-magnesia-silica.

<13>

The method for producing a fatty acid ester described in <11> or <12> in which the total pore volume of the porous structure is preferably 0.1 mL/g or more, more preferably 0.15 mL/g or more, further preferably 0.6 mL/g or more, furthermore preferably 0.9 mL/g or more, furthermore preferably 1 mL/g or more, furthermore preferably 1.1 mL/g or more, furthermore preferably 1.2 mL/g or more, furthermore preferably 2 mL/g or more, furthermore preferably 3 mL/g or more, and furthermore preferably 3.5 mL/g or more, and preferably 10 mL/g or less, furthermore preferably 7.5 mL/g or less, further preferably 7 mL/g or less, and furthermore preferably 5 mL/g or less.

<14>

The method for producing a fatty acid ester described in any one of <11> to <13> in which the volume of pores with a pore size of 0.1 µm or more and 500 µm or less in the porous structure is, based on the total pore volume, preferably 50% or more, more preferably 80% or more, further preferably 90% or more, and furthermore preferably 95% or more, and preferably 100% or less.

<15>

The method for producing a fatty acid ester described in any one of <11> to <14> in which the mode of the pore size of the porous structure is preferably 0.1 µm or more, more preferably 1 µm or more, further preferably 10 µm or more, and furthermore preferably 20 µm or more, and preferably 500 µm or less, more preferably 200 µm or less, further preferably 100 µm or less, and furthermore preferably 60 µm or less.

<16>

The method for producing a fatty acid ester described in any one of <11> to <15> in which the median of the pore size of the porous structure is preferably 0.1 µm or more, more preferably 1 µm or more, further preferably 10 µm or more, and furthermore preferably 20 µm or more, and preferably 500 µm or less, more preferably 200 µm or less, further preferably 140 µm or less, furthermore preferably 100 µm or less, and furthermore preferably 60 µm or less.

<17>

The method for producing a fatty acid ester described in any one of <11> to <16> in which the porosity of the porous structure is preferably 30% or more, more preferably 40% or more, further preferably 50% or more, furthermore preferably 55% or more, furthermore preferably 60% or more, and furthermore preferably 70% or more, and preferably 99% or less, more preferably 95% or less, and further preferably 93% or less.

<18>

The method for producing a fatty acid ester described in any one of <11> to <17> in which the bulk density of the porous structure is preferably 10 kg/m³ or more, more preferably 100 kg/m³ or more, and further preferably 150 kg/m³ or more, and preferably 7,000 kg/m³ or less, more preferably 4,000 kg/m³ or less, further preferably 2,400 kg/m³ or less, furthermore preferably 1,000 kg/m³ or less, furthermore preferably 500 kg/m³ or less, furthermore preferably 300 kg/m³ or less, and furthermore preferably 250 kg/m³ or less.

<19>

The method for producing a fatty acid ester described in any one of <11> to <18> in which the porous structure is preferably a fiber structure or a porous compact, and more preferably a fiber structure.

<20>

The method for producing a fatty acid ester described in any one of <11> to <19> in which the porous structure is a fiber structure, and the shape thereof is preferably a sheet, a tube, a honeycomb or an indefinite shape, and more preferably a sheet.

<21>

The method for producing a fatty acid ester described in any one of <11> to <20> in which the porous structure is a fiber structure, preferably woven fabric, knitted fabric or a nonwoven cloth, and more preferably a nonwoven cloth.

<22>

The method for producing a fatty acid ester described in any one of <1> to <21> in which the catalyst metal compound which is used for the catalyst and contained in the catalyst is an oxide.

<23>

The method for producing a fatty acid ester described in any one of <1> to <22> in which the catalyst is obtained by the following coating material preparation step, carrying step and calcining step:

the coating material preparation step: a step in which a catalyst precursor coating material or a catalyst metal oxide coating material is produced by dispersing a catalyst precursor or a catalyst metal oxide in a dispersion medium;

the carrying step: a step in which the catalyst precursor coating material or the catalyst metal oxide coating material obtained in the coating material preparation step is carried on the support; and the calcining step: a step in which the catalyst precursor or the catalyst metal oxide carried on the support in the carrying step is calcined.

<24>

The method for producing a fatty acid ester described in <23> in which the catalyst precursor is a compound which is converted to a catalyst metal oxide by calcining.

<25>

The method for producing a fatty acid ester described in <23> or <24> in which the carrying step is a carrying step by immersing the support in the catalyst precursor coating material or the catalyst metal oxide coating material.

<26>

The method for producing a fatty acid ester described in any one of <23> to <25> in which the catalyst precursor coating material or the catalyst metal oxide coating material contains a binder.

<27>

The method for producing a fatty acid ester described in <26> in which the binder is an oxide of a metal other than the catalyst metal.

<28>

The method for producing a fatty acid ester described in any one of <23> to <27> in which the concentration of the catalyst precursor or the catalyst metal oxide in the catalyst precursor coating material or the catalyst metal oxide coating material is preferably 1% by mass or more, more preferably 5% by mass or more, further preferably 15% by mass or more, and furthermore preferably 20% by mass or more, and preferably 40% by mass or less, more preferably 30% by mass or less, and further preferably 28% by mass or less.

<29>

The method for producing a fatty acid ester described in any one of <1> to <28> in which the catalyst metal is preferably Co, Ni or Cu, and more preferably Ni.

<30>

A method for producing an alcohol through desulfurization of sulfur from a fatty acid ester by the method for producing a fatty acid ester described in any one of <1> to <29> and hydrogenation of the obtained fatty acid ester.

<31>

The method for producing an alcohol described in <30> in which the hydrogenation of the fatty acid ester is conducted using a catalyst carrying a catalyst metal on a support, where the catalyst contains as the catalyst metal one or more elements selected from the elements of group 9, group 10 and group 11 of the periodic table, the total pore volume of the catalyst is 0.05 mL/g or more and the volume of pores with a pore size of 0.1 µm or more and 500 µm or less in the catalyst is 50% or more of the total pore volume.

<32>

A desulfurization method for desulfurization of sulfur from a fatty acid ester using a catalyst in which the catalyst carries a catalyst metal on a support, (a) the catalyst contains as the catalyst metal one or more elements selected from the elements of group 9, group 10 and group 11 of the periodic table, (b) the total pore volume of the catalyst is 0.05 mL/g or more, and (c) the volume of pores with a pore size of 0.1 µm or more and 500 µm or less is 50% or more of the total pore volume of the catalyst.

EXAMPLES

1. Evaluation Methods (1) Catalytic Activities (i) Measurement Method of Sulfur Concentration The sulfur concentration was measured using low level sulfur analyzer 9000LLS (manufactured by ANTEK Inc.) at a calcining temperature of 1050° C. and with the voltage of the UV detector set at 840 V.

With respect to palm kernel oil and coconut oil, 4.00 g of a sample was diluted with 5 mL of isooctane (manufactured by Kishida Chemical Co., Ltd.) and measured, and a fatty acid methyl ester was measured without diluting the fatty acid methyl ester.

(ii) Measurement Method of Alcohol Concentration

In Example 9, one drop of the reaction solution of hydrogenation was taken with a 2 mL disposable pipette, and 1 mL of trimethylsilylation (TMS) agent "TMSI-H" (manufactured by GL Sciences Inc.) was added thereto. The solution was diluted with 1.5 mL of hexane (manufactured by Kanto Chemical Co., Inc.) added thereto and filtered through a membrane filter with a pore size of 0.2 µm, and then gas chromatography (GC) analysis was conducted. The GC peak area percentage (%) was regarded as the alcohol concentration (% by mass) of the reaction solution.

GC measurement condition: "HP6890" (manufactured by Hewlett-Packard Development Company, L.P.)

Capillary column "Ultra-Alloy-1" 15 m, thickness 0.15 µm

Temperature 60° C. (2 minutes)→10° C./min→350° C. (15 minutes)

Split ratio 14:1, Inj temperature 300° C., Det temperature 350° C.

In Example 10, one drop of the reaction solution was put into a 10 mL sample bottle with a 2 mL disposable pipette and diluted with 1.5 mL of ethanol added thereto, and GC analysis was conducted. In Example 10, the total of GC area percentages (%) derived from methyl esters obtained by GC measurement was regarded as the concentration (% by mass). With respect to alcohols, the total of GC area percentages (%) derived from respective alcohols having 8 to 18 carbon atoms was regarded as the concentration (% by mass). With respect to hydrocarbons, the total of GC area percentages (%) derived from respective hydrocarbons having 12 to 18 carbon atoms was regarded as the concentration (% by mass).

GC measurement condition: "HP-6890" (manufactured by Hewlett-Packard Development Company, L.P.)

Capillary column

"HP-1" 30 m, thickness 0.25 μm, inside diameter 0.32 mm

Temperature 60° C. (0 minute)→8° C./min→300° C. (10 minutes)

Split ratio 9.1, Inj temperature 300° C., Det temperature 300° C.

(iii) Definitions of Catalytic Activities Per Mass of Catalyst Metal

When the reaction was conducted in a tubular reactor, the catalytic activity per mass of the catalyst metal (catalytic activity 1) was defined as follows.

Catalytic activity 1=log {(sulfur concentration before desulfurization)/(sulfur concentration after desulfurization)}/(mass of filled catalyst metal/volume of catalyst layer)

"Log" represents the natural logarithm.

When the reaction was conducted in an autoclave, the catalytic activity per mass of the catalyst metal (catalytic activity 2) was defined as follows.

Catalytic activity 2=log {(sulfur concentration at 0 hour of reaction)/(sulfur concentration after one hour of reaction)}/(charged Ni mass/charged liquid mass)

"Log" represents the natural logarithm.

The 0 hour of reaction means the time at which heating to the reaction temperature and pressurization to the reaction pressure were completed.

The sulfur concentration at 0 hour of reaction means the sulfur concentration of the reaction solution at 0 hour of reaction.

The sulfur concentration after one hour of reaction means the sulfur concentration of the reaction solution one hour after 0 hour of reaction.

(iv) Maintenance Rate of Catalytic Activity

As an indicator of the durability of the catalyst, the maintenance rate of the catalytic activity after passing a raw material liquid in an amount (mass) which was 1,500 times the amount of the catalyst metal through the catalyst layer was calculated by the following equation.

Maintenance rate of catalytic activity after passing 1,500 g-raw material/g-catalyst metal [%]=catalytic activity 1 after passing 1,500 g-raw material/g-catalyst metal÷catalytic activity 1 at 0 hour of reaction×100

The 0 hour of reaction means the time at which heating to the reaction temperature and pressurization to the reaction pressure were completed.

The "catalytic activity 1 after passing 1,500 g-raw material/g-catalyst metal" means the catalytic activity 1 after passing the raw material in an amount (mass) which was 1,500 times the amount of the catalyst metal through the reactor from 0 hour of reaction.

(2) Composition of Catalyst (i) Carried Amount of Catalyst Metal Per Unit Mass

The carried amount of the catalyst metal per unit mass of the catalyst [g/g] was quantified using X-ray fluorescence analyzer "Rigaku ZSX100e" (manufactured by Rigaku Corporation).

(ii) Carried Amount of Catalyst Metal Per Unit Volume

The carried amount of the catalyst metal per unit volume of the catalyst was calculated by the following equation.

Carried amount of catalyst metal per unit volume of catalyst [g/mL]=carried amount of catalyst metal per unit mass [g/g]×bulk density of catalyst [kg/m³]÷1,000

The bulk density of the catalyst was measured with the mercury porosimeter described in (4) (i) below.

(iii) Carried Amount of Catalyst Metal Oxide and Binder Per Unit Mass

Carried Amount of catalyst metal oxide and binder per unit mass [g/g]=(mass of catalyst after calcining [g]−mass of porous structure before carrying step [g])/mass of catalyst [g]

(iv) Carried Amount of Catalyst Metal Oxide and Binder Per Unit Volume

The carried amount of the catalyst metal oxide and the binder per unit volume of the catalyst carried on a porous ceramic support was calculated as follows.

Carried amount of catalyst metal oxide and binder per unit volume [g/mL]=carried amount of catalyst metal oxide and binder per unit mass [g/g]×bulk density of catalyst [kg/m³]÷1,000

The carried amount of the catalyst metal oxide and the binder per unit volume of the catalyst carried on an inorganic fiber support was calculated by the following equation.

Carried amount of catalyst metal oxide and binder per unit volume [g/mL]=carried mass of catalyst metal oxide and binder [g]÷volume of catalyst [mL]

The volume of the catalyst was calculated from the size of the catalyst measured using the ruler and calipers described in (5) below.

(3) Catalyst Precursor Coating Material

The particle size of the catalyst precursor particles in the catalyst precursor coating material was measured under the following condition using laser diffraction/scattering particle size distribution analyzer "LA-920" (manufactured by HORIBA, Ltd.).

Solvent: deionized water

Measurement condition: transmittance: 70 to 95%, stirring speed: level 2, refractive index: 1.16

(4) Pore Structure (i) Measurement Method of Pore Structure

The total pore volumes of the catalyst and the porous structure, the volumes of pores with a pore diameter of 0.1 μm or more and 500 μm or less per unit mass, the volumes of pores with a pore diameter of 0.02 μm or more and 0.2 μm or less per unit mass, the modes of the pore sizes, the medians of the pore sizes, the porosities, the specific surface areas and the bulk densities were measured using mercury porosimeter "AutoPoreIV9500" (manufactured by Micromeritics Instrument Corporation). The pressure range for the measurement was 0.6 psia to 31,000 psia.

(ii) Percentage of Volume of Pores with Pore Diameter of 0.1 μm or More and 500 μm or Less in Total Pore Volume The percentage of the volume or pores with a pore diameter of 0.1 μm or more and 500 μm or less in the total pore volume was calculated by the following equation.

Percentage of volume of pores with pore diameter of 0.1 μm or more and 500 μm or less in total pore volume=volume of pores with pore diameter of 0.1 μm or more and 500 μm or less [mL/g]÷total pore volume [mL/g]×100 [%]

(5) External Sizes
(i) Thicknesses of Fiber Structure and Catalyst Fiber Structure The thickness of the fiber structure was measured using constant-pressure thickness gauge "PG-11" (manufactured by Teclock Corporation) with a constant-pressure load of 0.363 N at a pressure of 0.363 kPa.

(ii) Measurement Method of External Sizes of Fiber Structure and Catalyst Fiber Structure Except for Thicknesses The external sizes of the catalyst and the porous structure other than the thicknesses were measured using a ruler and calipers.

2. Production Examples of Catalyst Precursor
(1) Production Example of Catalyst Precursor a Into a 2 L separable flask, 800 g of deionized water and 232 g of nickel nitrate hexahydrate (manufactured by Wako Pure Chemical Industries, Ltd.) were put, and the temperature was raised to 80° C. while stirring the mixture. The total amount of a solution which had been prepared by dissolving 33 g of water glass of JIS No. 3 (manufactured by Kishida Chemical Co., Ltd.) and 113 g of sodium carbonate (manufactured by Wako Pure Chemical Industries, Ltd.) in 630 g of deionized water and which had been heated to 80° C. was added thereto, while stirring the mixture. After the addition, 24 g of magnesium nitrate hexahydrate (manufactured by Wako Pure Chemical Industries, Ltd.) was added, and the generated slurry was stirred at 80° C. for an hour. Then, the solid component was separated from the slurry by filtration. The obtained solid component was washed with water and then dried at 110° C., and a catalyst precursor was obtained. The atomic ratio of Mg to Ni, Mg/Ni, which was calculated from the amounts of the raw materials was 1/8.5.

(2) Production Example of Catalyst Precursor b

First, in accordance with the method described in Example 5 of JP-A-5-177140, a catalyst precursor b carrying CuO, ZnO and BaO on $TiO_2$ was obtained. The generated precipitate was thoroughly washed with water, and then the solid component was dried in air atmosphere at atmospheric pressure at 110° C. The atomic ratio of the obtained catalyst precursor b was Cu/Zn/Ti/Ba=100/5.0/112.3/4.8.

3. Production Examples of Catalyst
(1) Porous Structures

The porous structures used as the supports in the Production Examples of the catalyst of the present application are as follows. The physical properties are shown in Table 1.

Ceramic spherical porous structure: "CAB-54" (manufactured by Iwao Jiki Kogyo Co., Ltd., outer diameter: 5 mm)

Calcia-magnesia-silica fiber sheet: "Superwool 607" (manufactured by Shin-Nippon Thermal Ceramics. Corporation)

Silica-alumina fiber sheet: "MC Paper" (manufactured by Nippon Sheet Glass Co. Ltd.)

TABLE 1

| | Ceramic spherical porous structure | Calcia-magnesia-silica fiber sheet | Silica-alumina fiber sheet |
|---|---|---|---|
| Bulk density [kg/m³] | 2318 | 199 | 208 |
| Mode of pore size [μm] | 91.2 | 52.0 | 22.7 |
| Median of pore size [μm] | 132 | 58.3 | 23.3 |
| Total pore volume [mL/g] | 0.165 | 3.60 | 4.43 |
| Porosity [%] | 38.1 | 71.9 | 92.1 |

TABLE 1-continued

| | Ceramic spherical porous structure | Calcia-magnesia-silica fiber sheet | Silica-alumina fiber sheet |
|---|---|---|---|
| Percentage of volume of pores with pore diameter of 0.1-500 μm in total pore volume [%] | 100.0 | 100.0 | 97.1 |

(2) Binders

The binder sol or the binders used in the Production Examples of the catalyst of the present application are as follows.

Alumina sol: "Aluminasol 200" (manufactured by Nissan Chemical Industries, Ltd., solid concentration: 10% by mass)

Silica sol: "Snowtex ST-20" (manufactured by Nissan Chemical Industries, Ltd., solid concentration: 20% by mass)

Alumina: alumina "Cataloid AP" (manufactured by JGC Catalysts and Chemicals Ltd.)

Titania sol: "AM-15" (manufactured by Taki Chemical Co., Ltd., solid concentration: 16.6% by mass)

Production Example 1 of Catalyst (i) Coating Material Preparation Step

In a 1 L plastic container, 80 g of the catalyst precursor a, 320 g of deionized water and 2 kg of zirconia balls with a diameter of 10 mm were enclosed, and the catalyst precursor a in the mixture was pulverized using a mill stage (manufactured by Tokyo Glass Kikai Corporation) at 200 rpm for five hours. The mode of the particle size of the catalyst precursor in the obtained catalyst precursor slurry was 7 μm.

A catalyst precursor slurry with a solid concentration of 2% by mass was obtained by mixing 100 g of the catalyst precursor slurry and 900 g of deionized water. To a recovery flask, 120 g of the catalyst precursor slurry and 1.2 g of the alumina sol were added, and a catalyst precursor coating material x with a solid concentration of 2% by mass was obtained. The ratio by mass of the solid component of the catalyst precursor a to the solid component of the binder in the catalyst precursor coating material x was 20/1.

(ii) Carrying Step

To the recovery flask in which the catalyst precursor coating material x was prepared, 55.8 g of the ceramic spherical porous structure was further added, and the ceramic spherical porous structure was immersed in the catalyst precursor coating material x. Then, the pores of the porous structure were deaerated by adjusting the pressure in the recovery flask to 300 Torr (absolute pressure) using an evaporator. Then, the temperature of an oil bath was raised to 120° C. to evaporate the water from the recovery flask, and the content was dried. Furthermore, 120 g of the catalyst precursor slurry and 1.2 g of the alumina sol were added to the recovery flask after drying, thereby preparing the catalyst precursor coating material x, and evaporation of water and drying using an evaporator were conducted five times under the above condition.

(iii) Calcining Step

The spherical porous structure carrying the catalyst precursor coating material obtained in the carrying step was calcined in air atmosphere at atmospheric pressure at 400° C. for two hours, and a catalyst A was obtained. The outer diameter of the catalyst A was 5 mm.

Production Example 2 of Catalyst (i) Coating Material Preparation Step

In a 250 mL plastic container, 36 g of the catalyst precursor a, 45 g of the silica sol, 58.5 g of deionized water, 10.5 g of isopropyl alcohol (manufactured by Kanto Chemical Co., Inc.) and 160 g of titania beads with a diameter of 0.8 mm were enclosed, and the mixture was treated using a disperser for test (JIS K5101-1-2, manufactured by Toyo Seiki Seisaku-sho, Ltd.) according to the method described in JIS K501-1-2 for 30 minutes, thereby obtaining a catalyst precursor coating material y with a solid concentration of 30% by mass. The ratio by mass of the solid component of the catalyst precursor a to the solid component of the binder was 80/20. The mode of the particle size of the catalyst precursor in the catalyst precursor coating material y was 1 µm.

(ii) Carrying Step

A Petri dish (φ 86 mm, height 14 mm) was filled with the catalyst precursor coating material y with a solid content of 30% by mass obtained in the coating material preparation step, and the calcia-magnesia-silica fiber sheet (20 mm×5 mm, thickness 1.0 mm) was immersed therein, turned over after 150 seconds and further immersed for 150 seconds, that is, the sheet was immersed for 300 seconds in total. The immersed fiber structure was dried on a stainless gauze with a sieve opening of 1 mm in air atmosphere at atmospheric pressure at 130° C. for 30 minutes.

(iii) Calcining Step

The calcining step was conducted under the same condition as in Production Example 1, and a catalyst B was obtained.

Production Example 3 of Catalyst

A catalyst C was obtained in the same manner as in Production Example 2, except that the size of the fiber sheet was 10 mm×2.5 mm and the thickness was 1.0 mm.

Production Example 4 of Catalyst (i) Coating Material Preparation Step

In a 50 mL plastic container, 11.2 g of the catalyst precursor a, 14.0 g of the silica sol, 6.4 g of deionized water and 3.4 g of polymeric surfactant "Kaocer" 2100 (manufactured by Kao Corporation) were enclosed, and the mixture was preliminarily mixed by shaking the container until blocks of powder disappeared.

Next, using thin-film spin system high-speed mixer "Filmix type 40-40" (manufactured by Primix Corporation), the mixture was stirred at a peripheral speed of 30 m/s for 30 seconds, and a catalyst precursor slurry with a solid concentration of 40% by mass containing the catalyst precursor a was obtained. The mode of the particle size of the catalyst precursor in the catalyst precursor slurry was 0.5 The catalyst precursor slurry was diluted with deionized water, and a catalyst precursor coating material z1 with a solid concentration of 20% by mass was obtained. The ratio by mass of the solid component of the catalyst precursor to the solid component of the binder was 80/20.

(ii) Carrying Step

A Petri dish (q 86 mm, height 14 mm) was filled with the catalyst precursor coating material z1, and the silica-alumina fiber sheet (50 mm×50 mm, thickness 1.0 mm) was immersed therein, turned over after 150 seconds and further immersed for 150 seconds, that is, the sheet was immersed for 300 seconds in total.

Then, the fiber structure impregnated with the catalyst precursor coating material z1 was placed on a stainless plate coated with polytetrafluoroethylene (230×230 mm, thickness 1.5 mm). A removing tool (a stainless plate, thickness 0.5 mm, width 75 mm) which was touching the surface of the fiber structure was moved once from one end to the other end, and thus the excess catalyst precursor coating material adhered on the surface of the fiber structure was removed. The fiber structure was turned over, and the same operation was conducted. Then, the fiber structure was dried on the stainless plate coated with polytetrafluoroethylene in air atmosphere at atmospheric pressure at 120° C. for 60 minutes.

(iii) Shaping Step

Next, the fiber structure was cut using a Thomson blade in such a manner that an area of 40 mm×40 mm was cut into 16 pieces each having a size of 20 mm×5 mm.

(iv) Calcining Step

The fiber sheet carrying the catalyst precursor coating material which had been cut into the size was calcined in air atmosphere at atmospheric pressure at 400° C. for five hours, and a catalyst E was obtained.

Production Example 5 of Catalyst

A catalyst F was obtained in the same manner as in Production Example 4, except that, in the coating material preparation step, a catalyst precursor coating material z2 with a solid concentration of 30% by mass was obtained by diluting the catalyst precursor slurry with deionized water.

Production Example 6 of Catalyst

A catalyst G was obtained in the same manner as in Production Example 4, except that, in the coating material preparation step, the catalyst precursor slurry was not diluted and a catalyst precursor coating material z3 with a solid concentration of 40% by mass was obtained.

Production Example 7 of Catalyst

A catalyst H was obtained in the same manner as in Production Example 4, except that, in the coating material preparation step, 2.8 g of the catalyst precursor a, 3.5 g of the silica sol and 28.7 g of deionized water were used and a catalyst precursor coating material w which had a solid concentration of 10% by mass and in which the ratio by mass of the solid component of the catalyst precursor to the solid component of the binder was 80/20 was obtained.

4. Comparative Production Examples of Catalyst

Comparative Production Example 1 of Catalyst

A catalyst D was obtained by mixing 3.56 g of the alumina as the binder with 100 g of the catalyst precursor a, molding the mixture into a noodle shape by extrusion molding and then conducting the calcining step under the same condition as in Production Example 1.

Comparative Production Example 2 of Catalyst

A catalyst I was obtained by mixing 4.65 g of the alumina as the binder with 100 g of the catalyst precursor a, molding the mixture into a noodle shape by extrusion molding and then conducting the calcining step under the same condition as in Production Example 4.

The physical properties of the catalysts A to I obtained in Production Examples 1 to 7 and Comparative Production Examples 1 and 2 are summarized in Table 2 and Table 3 below.

Production Examples of Hydrogenation Catalyst
(i) Coating Material Preparation Step In a 50 mL plastic container, 6.0 g of the catalyst precursor b, 9.0 g of the titania sol as the binder and 15.0 g of deionized water as the solvent were enclosed, and the mixture was preliminarily mixed by shaking the container until blocks of powder disappeared. Next, using thin-film spin system high-speed mixer "Filmix type 40-40" (manufactured by Primix Corporation), the mixture was treated at a peripheral speed of 30 m/s for 30 seconds, and a catalyst precursor coating material v in a slurry state with a solid content of 25% by mass was obtained. The ratio by mass of the solid component of the catalyst precursor to the solid component of the binder was 80/20. The particle size distribution of the catalyst precursor coating material v was measured by laser diffractometry, and the mode of the particle size of the catalyst precursor particles in the catalyst precursor coating material v was 1.8 μm.

(ii) Carrying Step

A Petri dish (ϕ 86 mm, height 14 mm) was filled with the catalyst precursor coating material v obtained in the coating material preparation step, and the silica-alumina fiber sheet (20 mm×5 mm, thickness 1.0 mm) was immersed therein, turned over after 150 seconds and further immersed for 150 seconds, that is, the sheet was immersed for 300 seconds in total. The immersed fiber structure was dried on a stainless plate coated with polytetrafluoroethylene (230 mm×230 mm, thickness 1.5 mm) in air atmosphere at atmospheric pressure at 120° C. for 60 minutes.

(iii) Calcining Step

The obtained fiber structure carrying the catalyst precursor coating material v was calcined in air atmosphere at atmospheric pressure at 400° C. for five hours, and a catalyst J was thus obtained. The physical properties of the obtained catalyst J are shown in Table 3.

TABLE 2

| | Catalyst | | | |
|---|---|---|---|---|
| | A | B | C | D |
| Molding method | Carried on porous ceramic carrier | Carried on inorganic fiber support | Carried on inorganic fiber support | Extrusion molded product |
| Carried amount of catalyst metal per unit volume [g/mL] | 0.0355 | 0.0885 | 0.191 | 0.698 |
| Carried amount of catalyst metal per unit mass [g/g] | 0.017 | 0.19 | 0.25 | 0.53 |
| Carried amount of catalyst metal oxide and binder per unit volume [g/mL] | 0.0599 | 0.244 | 0.391 | — |
| Percentage of volume of pores with pore diameter of 0.1-500 μm in total pore volume [%] | 96.7 | 94.7 | 83.9 | 13.7 |
| Mode of pore size [μm] | 60.6 | 60.7 | 52.0 | 0.0448 |
| Median of pore size [μm] | 47.5 | 64.0 | 33.7 | 0.0491 |
| Total pore volume [mL/g] | 0.176 | 1.53 | 0.916 | 0.379 |
| Volume of pores with pore diameter of 0.02-0.2 μm [mL/g] | 0.008 | 0.01 | 0.086 | 0.296 |
| Porosity [%] | 36.8 | 71.5 | 69.9 | 49.9 |
| Specific surface area [m$^2$/g] | 0.889 | 37.9 | 37.2 | 45.6 |
| Bulk density [kg/m$^3$] | 2089 | 466 | 764 | 1317 |

TABLE 3

| Catalyst | E | F | G | H | I | J |
|---|---|---|---|---|---|---|
| Molding method | Carried on inorganic fiber support | Carried on inorganic fiber support | Carried on inorganic fiber support | Carried on inorganic fiber support | Extrusion molded product | Carried on inorganic fiber support |
| Carried amount of catalyst metal per unit volume [g/mL] | 0.0708 | 0.129 | 0.235 | 0.0295 | 0.799 | 0.12 |
| Carried amount of catalyst metal per unit mass [g/g] | 0.21 | 0.28 | 0.32 | 0.13 | 0.57 | 0.27 |
| Carried amount of catalyst metal oxide and binder per unit volume [g/mL] | 0.155 | 0.256 | 0.447 | 0.0675 | — | 1.04 |
| Percentage of volume of pores with pore diameter of 0.1-500 μm in total pore volume [%] | 95.5 | 89.7 | 77.2 | 98.0 | 10.5 | 95.9 |
| Mode of pore size [μm] | 19.1 | 21.3 | 21.3 | 19.1 | 0.0501 | 12.1 |
| Median of pore size [μm] | 20.5 | 19.7 | 6.38 | 20.5 | 0.0452 | 10.02 |
| Total pore volume [mL/g] | 2.45 | 1.35 | 0.777 | 3.16 | 0.422 | 1.86 |
| Volume of pores with pore diameter of 0.02-0.2 μm [mL/g] | 0.065 | 0.069 | 0.080 | 0.054 | 0.300 | |
| Porosity [%] | 82.6 | 62.2 | 57.1 | 71.6 | 59.2 | 84.3 |
| Specific surface area [m$^2$/g] | 29.9 | 37.4 | 53.7 | 15.1 | 87.0 | 14.8 |
| Bulk density [kg/m$^3$] | 337 | 462 | 735 | 227 | 1403 | 452.2 |

Example 1

(i) Reduction

The catalyst A was reduced in a gas phase at 450° C. at atmospheric pressure in a hydrogen atmosphere of 4% by volume for 5 hours and then stabilized at 25° C. at atmospheric pressure in an oxygen atmosphere of 1% by volume for eight hours. A tubular reactor with an inside diameter of 13 mm was filled with the stabilized catalyst A in such a manner that the volume of the catalyst layer became 12 mL, and reduction was conducted in a liquid phase under the condition of gauge pressure of 19.6 MPa, 155° C., a flow rate of a fatty acid methyl ester derived from palm kernel oil of 18.2 g/h and a hydrogen flow rate of 44.2 NL/h, for 24 hours.

(ii) Desulfurization

After the completion of the reduction, the fatty acid methyl ester derived from palm kernel oil was switched to refined palm kernel oil (sulfur concentration=2.6 mg/kg), and desulfurization of the refined palm kernel oil was conducted in the tubular reactor by fixed bed continuous process. The reaction condition was 19.6 MPa (gauge pressure), 155° C., a flow rate of the raw material of 54 g/h (LHSV=5 Hr$^{-1}$) and a hydrogen flow rate of 132 NL/h (25 times by mole based on the ester group). The sulfur concentration of the reaction solution was measured at 0 hour of reaction and after passing the fatty acid methyl ester in an amount (mass) which was 1,500 times the amount of the catalyst metal, and the catalytic activities 1 and the maintenance rates of the catalytic activity at the respective points were calculated.

Example 2

Desulfurization was conducted in the same manner as in Example 1, except that the catalyst C was used and the sulfur concentration of the raw material was 1.7 mg/kg.

Comparative Example 1

Desulfurization was conducted in the same manner as in Example 1, except that the catalyst D was used and the sulfur concentration of the raw material was 2.1 mg/kg.

The results of the desulfurization of Examples 1 and 2 and Comparative Example 1 are shown in Table 4. It can be said that, in the Examples according to the present invention, the catalytic activities per mass of the catalyst metal in the catalyst have improved as compared to the Comparative Example. Moreover, it can be said that the maintenance rates of the catalytic activity have also improved.

TABLE 4

|  | Example 1 | Example 2 | Comparative Example 1 |
| --- | --- | --- | --- |
| Catalyst | A | C | D |
| Molding method | Carried on porous ceramic support | Carried on inorganic fiber support | Extrusion molded product |
| Raw reaction material | Refined palm kernel oil | Refined palm kernel oil | Refined palm kernel oil |
| Ni filling amount [g-Ni/cm$^3$-bed] | 0.0179 | 0.0650 | 0.413 |
| Catalytic activity 1 at 0 hour of reaction | 19.9 | 32.3 | 7.93 |

TABLE 4-continued

|  | Example 1 | Example 2 | Comparative Example 1 |
| --- | --- | --- | --- |
| Catalytic activity 1 after passing 1,500 g-raw material/g-catalyst metal | 14.6 | 22.4 | 3.05 |
| Maintenance rate of catalytic activity after passing 1,500 g-raw material/g-catalyst metal [%] | 73.4 | 69.3 | 38.5 |

Example 3

(i) Reduction

The catalyst A was reduced and stabilized in a gas phase under the same condition as in Example 1. A 500 mL autoclave was filled with the stabilized catalyst A and 200 g of lauryl alcohol "Kalcol 2098" (manufactured by Kao Corporation) in such a manner that the Ni concentration became 0.016% by mass based on lauryl alcohol, and the atmosphere in the autoclave was replaced with hydrogen. Under the condition of 1.0 MPa (gauge pressure), 200° C. and a stirring speed of 900 rpm, reduction was conducted in a liquid phase with a hydrogen flow of 5 NL/min for two hours.

(ii) Desulfurization

After the completion of the reduction, lauryl alcohol was replaced with a fatty acid methyl ester derived from palm kernel oil (distilled product, sulfur concentration=0.88 mg/kg), and the atmosphere in the autoclave was replaced with hydrogen. Then, desulfurization of 200 g of the fatty acid ester was conducted by batch process. The reaction condition was 24.5 MPa (gauge pressure), 135° C., a stirring speed of 900 rpm and a hydrogen flow rate of 5 NL/min. The sulfur concentration of the reaction solution was measured at 0 hour of reaction and one hour after 0 hour of reaction, and the catalytic activity 2 was calculated.

Example 4

The reaction was conducted under the same condition as in Example 3, except that the catalyst B was used and the sulfur concentration of the raw material was different (sulfur concentration=0.43 mg/kg).

Comparative Example 2

The reaction was conducted under the same condition as in Example 3, except that the catalyst D was used and the Ni concentration was 0.53% by mass based on the charged liquid mass.

The results of the desulfurization of Examples 3 and 4 and Comparative Example 2 are shown in Table 5. It can be said that, in the Examples according to the present invention, the catalytic activities per mass of the catalyst metal in the catalyst have improved as compared to the Comparative Example.

TABLE 5

|  | Example 3 | Example 4 | Comparative Example 2 |
| --- | --- | --- | --- |
| Catalyst | A | B | D |
| Molding method | Carried on porous ceramic support | Carried on inorganic fiber support | Extrusion molded product |

TABLE 5-continued

|  | Example 3 | Example 4 | Comparative Example 2 |
|---|---|---|---|
| Raw reaction material | Methyl ester derived from palm kernel oil | Methyl ester derived from palm kernel oil | Methyl ester derived from palm kernel oil |
| Catalytic activity 2 | 7910 | 7461 | 351 |
| Catalytic activity 2 (relative value) | 22.5 | 21.3 | 1.0 |

Examples 5 to 8

(i) Reduction

The catalysts E to H were each reduced under the same condition as in Example 3, except that 500 mL autoclaves were filled with the catalysts E to H which had been stabilized under the same condition as in Example 1 in such a manner that the Ni concentration became 0.15% by mass based on lauryl alcohol.

(ii) Desulfurization

After the completion of the reduction, lauryl alcohol was replaced with unrefined coconut oil (sulfur concentration=3.5 mg/kg), and the atmosphere in the autoclaves was replaced with hydrogen. Then, desulfurization of 200 g of the unrefined coconut oil was conducted by batch process. The reaction condition was 2.0 MPa (gauge pressure), 170° C., a stirring speed of 900 rpm and hydrogen 5 NL/min. The catalytic activities 2 were calculated in the same manner as in Example 3.

Comparative Example 3

The reaction was conducted under the same condition as in Examples 5 to 8, except that the catalyst I was used.

The results of the desulfurization of Examples 5 to 8 and Comparative Example 3 are shown in Table 6. It can be said that, in the Examples according to the present invention, the catalytic activities per mass of the catalyst metal in the catalyst have improved as compared to the Comparative Example.

TABLE 6

|  | Example 5 | Example 6 | Example 7 | Example 8 | Comparative Example 3 |
|---|---|---|---|---|---|
| Catalyst | E | F | G | H | I |
| Molding method | Carried on inorganic fiber support | Carried on inorganic fiber support | Carried on inorganic fiber support | Carried on inorganic fiber support | Extrusion molded product |
| Raw reaction material | Unrefined coconut oil | Unrefined coconut oil | Unrefined coconut oil | Unrefined coconut oil | Unrefined coconut oil |
| Catalytic activity 2 | 939 | 1124 | 453 | 702 | 246 |
| Catalytic activity 2 (relative value) | 3.8 | 4.6 | 1.8 | 2.9 | 1.0 |

<Example 9> (Alcohol Production)

(i) Reduction

Reduction was conducted under the same condition as in Example 3, except that a 500 mL autoclave was filled with the catalyst A which had been reduced and stabilized in a gas phase under the same condition as in Example 1 in such a manner that the Ni concentration became 0.14% by mass based on lauryl alcohol.

(ii) Desulfurization

After the completion of the reduction, desulfurization was conducted under the same condition as in Example 3, except that lauryl alcohol was replaced with refined coconut oil (sulfur concentration=2.6 mg/kg) and desulfurization of 200 g of the fatty acid ester was conducted by batch process. The sulfur concentration of the reaction solution was measured at 0 hour of reaction and one hour after 0 hour of reaction, and the catalytic activity 2 was calculated. The catalytic activity 2 was 504.

(iii) Hydrogenation

Next, a 500 mL autoclave was filled with 6.0 g of Cu—Cr catalyst "KSC-1" (manufactured by JGC Catalysts and Chemicals Ltd.) and the coconut oil obtained by the desulfurization, and the atmosphere in the autoclave was replaced with hydrogen. Then, hydrogenation of 120 g of the coconut oil was conducted. The reaction condition was 24.5 MPa (gauge pressure), 250° C., a stirring speed of 900 rpm and a hydrogen flow rate of 5 NL/min. After reacting for five hours after the completion of heating to the reaction temperature and pressurization to the reaction pressure, the alcohol content in the reaction solution was 96.1%, and the saponification value was 2.7 mg-KOH/g.

<Example 10> (Alcohol Production)

(i) Reduction of Desulfurization Catalyst

The catalyst C was reduced and stabilized in a gas phase under the same condition as in Example 1. A 500 mL autoclave was filled with the stabilized catalyst C and 240 g of lauryl alcohol "Kalcol 2098" (manufactured by Kao Corporation) in such a manner that the Ni concentration became 0.016% by mass based on lauryl alcohol, and the atmosphere in the autoclave was replaced with hydrogen. Under the condition of 1.0 MPa (gauge pressure), 200° C. and a stirring speed of 900 rpm, reduction was conducted in a liquid phase with a hydrogen flow of 5 NL/min for two hours.

(ii) Desulfurization

After the completion of the reduction, lauryl alcohol was replaced with a fatty acid methyl ester derived from palm kernel oil (distilled product, sulfur concentration=0.47 mg/kg), and the atmosphere in the autoclave was replaced with hydrogen. Then, desulfurization of 240 g of the fatty acid ester was conducted by batch process. The reaction condition was 24.5 MPa (gauge pressure), 135° C., a stirring speed of 900 rpm and a hydrogen flow rate of 5 NL/min, and the reaction was conducted for two hours. The sulfur concentration of the reaction solution was measured at 0 hour of reaction and one hour after 0 hour of reaction, and the calculated catalytic activity 2 was 2818.

(iii) Reduction of Hydrogenation Catalyst

A 500 mL autoclave was filled with 3.81 g of the catalyst J and 200 g of lauryl alcohol "Kalcol 2098" (manufactured by Kao Corporation), and the atmosphere in the autoclave was replaced with hydrogen. Then, the catalyst was reduced by batch process. The reaction condition was 1.0 MPa (gauge pressure), 200° C., a stirring speed of 900 rpm and a hydrogen flow rate of 5 NL/min. The reduction was conducted for two hours with the point at which heating and pressurization were completed set as reaction time of 0 hour.

(iv) Hydrogenation

After the completion of the reduction, lauryl alcohol was replaced with the fatty acid methyl ester obtained through the desulfurization (sulfur concentration=0.21 mg/kg), and the atmosphere in the autoclave was replaced with hydrogen. Then, 160 g of the methyl ester was hydrogenated by batch process. The reaction condition was 22.5 MPa (gauge pressure), 250° C., a stirring speed of 900 rpm and a hydrogen flow rate of 5 NL/min. The reaction was conducted with the point at which heating and pressurization were completed set as reaction time of 0 hour. During the reaction, samples were taken from the reaction solution, and the liquid composition was analyzed. At the reaction time of 0.5 hours, the alcohol content in the reaction solution was 28.4%, and the hydrocarbon content was 0.015%. At the reaction time of 1.0 hour, the alcohol content in the reaction solution was 42.7%, and the hydrocarbon content was 0.028%. It was possible to conduct hydrogenation in which the amount of hydrocarbons as by-products was low and which was excellent in selectivity.

The invention claimed is:

1. A method for producing a fatty acid ester through desulfurization of sulfur from a fatty acid ester using a catalyst,
   wherein the catalyst carries a catalyst metal on a support,
   (a) the catalyst contains as the catalyst metal one or more elements selected from the elements of group 9, group 10 and group 11 of the periodic table,
   (b) the total pore volume of the catalyst is 0.05 mL/g or more, and
   (c) the volume of pores with a pore size of 0.1 µm or more and 500 µm or less is 50% or more of the total pore volume of the catalyst.

2. The method for producing a fatty acid ester according to claim 1, wherein the volume of pores with a pore size of 0.1 µm or more and 500 µm or less in the catalyst is 70% or more of the total pore volume.

3. The method for producing a fatty acid ester according to claim 1, wherein the porosity of the catalyst is 30% or more and 99% or less.

4. The method for producing a fatty acid ester according to claim 1, wherein the median of the pore size of the catalyst is 0.1 µm or more and 100 µm or less.

5. The method for producing a fatty acid ester according to claim 1, wherein the carried amount of the catalyst metal per unit volume of the catalyst is 0.02 g/mL or more and 1.0 g/mL or less.

6. The method for producing a fatty acid ester according to claim 1, wherein the carried amount of the catalyst metal per unit mass of the catalyst is 0.01 g/g or more and 0.7 g/g or less.

7. The method for producing a fatty acid ester according to claim 1, wherein the support has a porous structure.

8. The method for producing a fatty acid ester according to claim 1, wherein the support is a fiber structure.

9. The method for producing a fatty acid ester according to claim 1, wherein the catalyst is obtained by the following coating material preparation step, carrying step and calcining step:
   the coating material preparation step: a step in which a catalyst precursor coating material or a catalyst metal oxide coating material is produced by dispersing a catalyst precursor or a catalyst metal oxide in a dispersion medium;
   the carrying step: a step in which the catalyst precursor coating material or the catalyst metal oxide coating material obtained in the coating material preparation step is carried on the support; and
   the calcining step: a step in which the catalyst precursor or the catalyst metal oxide carried on the support in the carrying step is calcined.

10. The method for producing a fatty acid ester according to claim 9, wherein the catalyst precursor is a compound which is converted to a catalyst metal oxide by calcining.

11. The method for producing a fatty acid ester according to claim 9, wherein the carrying step is a carrying step by immersing the support in the catalyst precursor coating material or the catalyst metal oxide coating material.

12. The method for producing a fatty acid ester according to claim 9, wherein the catalyst precursor coating material or the catalyst metal oxide coating material contains a binder.

13. The method for producing a fatty acid ester according to claim 12, wherein the binder is an oxide of a metal other than the catalyst metal.

14. The method for producing a fatty acid ester according to claim 1, wherein the catalyst metal is one or more elements selected from Co, Ni and Cu.

15. A method for producing an alcohol through desulfurization of sulfur from a fatty acid ester using a catalyst and hydrogenation of the obtained fatty acid ester,
   wherein the catalyst carries a catalyst metal on a support,
   (a) the catalyst contains as the catalyst metal one or more elements selected from the elements of group 9, group 10 and group 11 of the periodic table,
   (b) the total pore volume of the catalyst is 0.05 mL/g or more, and
   (c) the volume of pores with a pore size of 0.1 µm or more and 500 µm or less is 50% or more of the total pore volume of the catalyst.

16. The method for producing an alcohol according to claim 15,
   wherein the hydrogenation of the fatty acid ester is conducted using a catalyst carrying a catalyst metal on a support,
   wherein the catalyst contains one or more elements selected from the elements of group 9, group 10 and group 11 of the periodic table, the total pore volume of the catalyst is 0.05 mL/g or more, and the volume of pores with a pore size of 0.1 µm or more and 500 µm or less in the catalyst is 50% or more of the total pore volume.

17. A desulfurization method for desulfurization of sulfur from a fatty acid ester using a catalyst,
   wherein the catalyst carries a catalyst metal on a support,
   (a) the catalyst contains as the catalyst metal one or more elements selected from the elements of group 9, group 10 and group 11 of the periodic table,
   (b) the total pore volume of the catalyst is 0.05 mL/g or more, and
   (c) the volume of pores with a pore size of 0.1 µm or more and 500 µm or less is 50% or more of the total pore volume of the catalyst.

* * * * *